US012614621B2

(12) United States Patent
Rapchak et al.

(10) Patent No.: US 12,614,621 B2
(45) Date of Patent: Apr. 28, 2026

(54) MEDICATION THERAPY MANAGEMENT SYSTEM AND METHODS

(71) Applicant: Leap of Faith Technologies, Inc., Libertyville, IL (US)

(72) Inventors: Barbara Rapchak, Batavia, IL (US); Frank Naeymi-Rad, Libertyville, IL (US); David Haines, Arlington Heights, IL (US); John Trzesniak, Westmont, IL (US)

(73) Assignee: Leap of Faith Technologies, Inc., Libertyville, IL (US)

( * ) Notice: Subject to any disclaimer, the term of this patent is extended or adjusted under 35 U.S.C. 154(b) by 165 days.

(21) Appl. No.: 18/634,608

(22) Filed: Apr. 12, 2024

(65) Prior Publication Data

US 2024/0355445 A1      Oct. 24, 2024

Related U.S. Application Data

(60) Provisional application No. 63/496,267, filed on Apr. 14, 2023.

(51) Int. Cl.
G16H 20/10        (2018.01)
G16H 10/20        (2018.01)
(Continued)

(52) U.S. Cl.
CPC ............. G16H 20/10 (2018.01); G16H 10/20 (2018.01); G16H 10/60 (2018.01); G16H 15/00 (2018.01); G16H 50/20 (2018.01)

(58) Field of Classification Search
CPC ........ G16H 20/10; G16H 10/60; G16H 15/00; G16H 50/20; G16H 10/20
See application file for complete search history.

(56) References Cited

U.S. PATENT DOCUMENTS 5,748,872 A  *  5/1998  Norman .................. G02F 1/135
                                                   714/6.32
5,819,257 A  *  10/1998  Monge .............. G06F 16/24566
(Continued)

OTHER PUBLICATIONS

Ayatollahi, HIR, 2019, pp. 289-296.*
(Continued)

*Primary Examiner* — Michael I Ezewoko
(74) *Attorney, Agent, or Firm* — Lathrop GPM LLP; Alex Shtraym

(57)        ABSTRACT

The invention relates generally to medication therapy and more particularly to a system and methods for medication therapy management to support improved adherence and alert clinicians of changes in behavior or symptoms. The system may facilitate interactions between various data sources (e.g., medical health records, genomics databases, and other connected third-party devices) to manage workflow, execute rules, interface with knowledge bases, codify information, schedule events, provide notification, and more. In addition, the system may include a conversational or actionable artificial intelligence persona tailored to each user and configured to, for example, converse, instruct, and/or coach a user according to one or more features of the system. Advantageously, the system may improve adherence and facilitate patient engagement, care transition, and disease management, resulting in, for example, reduced healthcare costs for providers and payers, and enhanced drug use for pharmaceutical manufacturers, pharmacies, and specialty pharmacies.

19 Claims, 14 Drawing Sheets

600

602
602
612
606
608
610

(51) Int. Cl.
  *G16H 10/60* (2018.01)
  *G16H 15/00* (2018.01)
  *G16H 50/20* (2018.01)

(56) References Cited

U.S. PATENT DOCUMENTS

| | | | | | |
|---|---|---|---|---|---|
| 5,903,889 | A * | 5/1999 | de la Huerga | ........ | G06F 40/134 |
| 5,931,900 | A * | 8/1999 | Notani | ................... | G06Q 10/06 |
| | | | | | 709/201 |
| 6,006,233 | A * | 12/1999 | Schultz | .............. | G06F 16/2246 |
| 6,029,162 | A * | 2/2000 | Schultz | .............. | G06F 16/2246 |
| 6,078,924 | A * | 6/2000 | Ainsbury | ................ | G06F 16/34 |
| | | | | | 707/E17.093 |
| 6,105,035 | A * | 8/2000 | Monge | ................. | G06F 16/289 |
| | | | | | 707/999.102 |
| 6,115,715 | A * | 9/2000 | Traversat | ................ | G06F 9/466 |
| | | | | | 717/121 |
| 6,122,636 | A * | 9/2000 | Malloy | ................. | G06F 16/284 |
| | | | | | 707/999.102 |
| 6,167,406 | A * | 12/2000 | Hoskins | ................. | G06F 16/21 |
| | | | | | 715/767 |
| 6,192,371 | B1 * | 2/2001 | Schultz | ................ | G06F 16/289 |
| | | | | | 345/646 |
| 6,246,794 | B1 * | 6/2001 | Kagehiro | ............ | G06V 30/262 |
| | | | | | 382/229 |
| 6,345,268 | B1 * | 2/2002 | de la Huerga | ........ | G16H 40/63 |
| | | | | | 707/999.102 |
| 6,345,278 | B1 * | 2/2002 | Hitchcock | ............ | G06F 40/174 |
| | | | | | 707/999.102 |
| 6,405,211 | B1 * | 6/2002 | Sokol | ..................... | G06F 40/258 |
| | | | | | 707/999.102 |
| 6,523,009 | B1 * | 2/2003 | Wilkins | ................ | G16H 10/65 |
| | | | | | 705/2 |
| 6,643,652 | B2 * | 11/2003 | Helgeson | .............. | G06F 16/258 |
| 6,662,188 | B1 * | 12/2003 | Rasmussen | .......... | G06F 16/289 |
| | | | | | 707/999.102 |
| 6,708,186 | B1 * | 3/2004 | Claborn | ................ | G06F 16/289 |
| | | | | | 707/999.102 |
| 6,721,747 | B2 * | 4/2004 | Lipkin | ................ | G06F 16/9535 |
| | | | | | 709/200 |
| 6,901,398 | B1 * | 5/2005 | Horvitz | ................ | G06Q 10/107 |
| | | | | | 707/999.005 |
| 6,987,221 | B2 * | 1/2006 | Platt | ..................... | G10H 1/0058 |
| | | | | | 707/999.102 |
| 7,734,656 | B2 * | 6/2010 | Bessette | ................. | H04L 67/01 |
| | | | | | 705/2 |
| 7,974,924 | B2 * | 7/2011 | Holla | ........................ | H04L 9/14 |
| | | | | | 705/51 |
| 8,751,501 | B2 * | 6/2014 | Naeymi-Rad | .......... | G16H 40/20 |
| | | | | | 707/738 |
| 8,984,017 | B2 * | 3/2015 | Naeymi-Rad | .......... | G16H 10/60 |
| | | | | | 707/810 |
| 10,311,388 | B2 * | 6/2019 | Olsen | ..................... | G16H 70/20 |
| 10,395,330 | B2 * | 8/2019 | Dorris | ..................... | G16H 20/10 |
| 10,437,957 | B2 * | 10/2019 | Cox | ......................... | G06N 20/00 |
| 10,474,971 | B2 * | 11/2019 | Olsen | ............ | G06Q 10/063112 |
| 10,528,702 | B2 * | 1/2020 | Cox | ..................... | G16H 40/63 |
| 10,558,785 | B2 * | 2/2020 | Cox | ..................... | G16H 40/67 |
| 10,565,309 | B2 * | 2/2020 | Cox | ..................... | G16H 40/20 |
| 10,585,916 | B1 * | 3/2020 | Burton | ................. | G06F 16/254 |
| 10,685,089 | B2 * | 6/2020 | Dorris | ................... | G16H 20/40 |
| 10,923,231 | B2 * | 2/2021 | Kelly | ..................... | G16H 40/67 |
| 10,937,526 | B2 * | 3/2021 | Cox | ..................... | G06F 16/2477 |
| 11,037,658 | B2 * | 6/2021 | Cox | ..................... | G16H 40/67 |
| 11,037,682 | B2 * | 6/2021 | Kelly | ..................... | G16H 50/30 |
| 11,200,521 | B2 * | 12/2021 | Olsen | ..................... | G16H 70/00 |
| 11,373,736 | B2 * | 6/2022 | Li | ........................... | G16Z 99/00 |
| 11,769,571 | B2 * | 9/2023 | Cox | ..................... | G06F 40/279 |
| | | | | | 705/2 |
| 11,824,937 | B2 * | 11/2023 | Goodman | ............... | H04L 67/12 |
| 11,886,686 | B2 * | 1/2024 | Gold | ..................... | G06F 3/0483 |
| 2001/0051880 | A1 * | 12/2001 | Schurenberg | .......... | G16H 10/40 |
| | | | | | 705/3 |
| 2002/0007284 | A1 * | 1/2002 | Schurenberg | .......... | G16H 10/60 |
| | | | | | 705/2 |
| 2002/0010679 | A1 * | 1/2002 | Felsher | ............... | G06F 21/6245 |
| | | | | | 705/51 |
| 2002/0169788 | A1 * | 11/2002 | Lee | ........................ | G06F 16/986 |
| | | | | | 707/E17.118 |
| 2003/0036683 | A1 * | 2/2003 | Kehr | ....................... | G16H 70/20 |
| | | | | | 600/300 |
| 2003/0115084 | A1 * | 6/2003 | Gage | ................... | G06F 21/6245 |
| | | | | | 705/2 |
| 2004/0172307 | A1 * | 9/2004 | Gruber | ................... | G16H 10/60 |
| | | | | | 705/3 |
| 2005/0108052 | A1 * | 5/2005 | Omaboe | ............... | G16H 40/20 |
| | | | | | 705/2 |
| 2007/0271313 | A1 * | 11/2007 | Mizuno | ............... | G06F 11/1662 |
| 2008/0172737 | A1 * | 7/2008 | Shen | ....................... | G16H 10/60 |
| | | | | | 726/21 |
| 2008/0221920 | A1 * | 9/2008 | Courtney | ............... | G16H 10/65 |
| | | | | | 705/2 |
| 2008/0262868 | A1 * | 10/2008 | Malolepszy | ........... | G16H 10/65 |
| | | | | | 705/2 |
| 2008/0312959 | A1 * | 12/2008 | Rose | ....................... | G16H 10/60 |
| | | | | | 705/2 |
| 2009/0222286 | A1 * | 9/2009 | Elsholz | .................. | G16H 10/60 |
| | | | | | 707/999.1 |

OTHER PUBLICATIONS

Srivani, Elsevier, Feb. 2023, pp. 1-24.*
Dolin et al., Introducing HL7 FHIR Genomics Operations: a developer-friendly approach to genomics-EHR integration. Journal of the American Medical Informatics Association, vol. 30, Issue 3, Mar. 2023, pp. 485-493, https://doi.org/10.1093/jamia/ocac246.

* cited by examiner

1 – Takes medication as prescribed
0 – Does not take medication as prescribed
2 – Patient reports outcomes, adverse events (AE)
3 – PRO/AE require provider intervention
4 – Provider engages with patient
5 – End therapy (provider directive or therapy plan completed)

MEDICATION THERAPY MANAGEMENT SYSTEM AND METHODS

RELATED APPLICATIONS

This application is a nonprovisional application which claims priority to U.S. Provisional Application No. 63/496,267, filed on Apr. 14, 2023, and is incorporated by reference in its entirety.

FIELD OF THE INVENTION

The invention relates generally to medication therapy and more particularly to a system and methods for medication therapy management to support improved adherence and alert clinicians of changes in behavior or symptoms.

BACKGROUND

Healthcare providers often rely on stand-alone information systems for medication therapy purposes. Traditionally, physicians prescribe, pharmacists dispense, and nurses administer and care for patients. As a result, a particular prescription decision may be based solely on one prescriber's clinical judgment. This is further complicated by the fact that patients frequently have multiple physicians, and often, multiple pharmacies that, more likely than not, do not know what the others are prescribing or dispensing.

Further, conventional systems generally are not configured to monitor adherence to a medication therapy. Generally, less than half of patients take their doses as prescribed and one in three patients will discontinue treatment before their first refill is due. Further, non-adherence to medication therapy is a leading cause of hospital admissions.

In an attempt to address a patient's failures to adhere to a medication therapy, conventional systems may be configured to provide reminders and alerts for taking medication and for refilling prescriptions. Such systems, however, lack personal interaction, including those between a medical professional and the patient at clinically relevant times. Moreover, conventional systems often fail to record outcomes related to adherence or lack thereof.

Therefore, a need exists for a medication therapy system and methods for supporting improved adherence and facilitating patient engagement, care transition, and disease management efficiently and effectively.

SUMMARY

The invention relates to a system and methods for medication therapy management to support improved adherence and alert clinicians of changes in behavior or symptoms. Advantageously, the system may improve adherence and facilitate patient engagement, care transition, and disease management.

In one aspect, the system may be configured to access a patient's medical record including, for example, clinical data and genomic data. The medical record may further include information relating to adherence, patient behavior, and the like.

Using the medical record, the system may generate and analyze a structured data set. The structured data set may identify one or more orders (e.g., a scheduled medication or therapy plan) corresponding to a diagnosis or symptoms of the patient. Based on an analysis of the structured data set, the system may be configured to create one or more events. By generating events, the system may provide a patient with auditory and textual notifications directed to when, what, and how to take their medications. Generated events may also facilitate verifying and tracking the patient's symptoms and general health.

The system may also be configured to dynamically generate code for creating events in response to identifying the one or more orders. The generated code may include questionnaires corresponding to the patient, the one or more orders, and/or the diagnosis. Further, the generated code may correspond to one or more connected devices, such as a wearable device configured to monitor one or more characteristics of a user's health.

In response to receiving an input corresponding to the one or more created events, the system may detect a state of the patient. Inputs may be received from the user or retrieved by the system from another device. For instance, the system may retrieve, from a connected device, behavior data, such as information corresponding to a patient's diet, emotional state, sleep, and exercise. Based on the input, the system may detect whether the patient is adherent or non-adherent to a medication therapy plan. Additional states detected by the system may include adverse events, provider intervention required, need for additional analysis, and/or end of treatment.

The system may then output an interface corresponding to the patient's medical record, the one or more events, and/or the patient's detected state. For instance, the interface may include a care management dashboard having various interactive components and information, such as severity and management status, categorized problems lists and past medical history, allergy intolerance, and social and family history. The system may also output a conversational or actionable artificial intelligence persona configured to perform cognitive analysis and artificial intelligence processes to converse, instruct, and/or coach a user according to one or more features of system 100 described above, such as patient-specific information, medication information, treatment adherence, corrective actions, scheduling, and the like.

While the invention is susceptible to various modifications and alternative forms, specific exemplary embodiments thereof have been shown by way of example in the drawings and have herein been described in detail. It should be understood, however, that there is no intent to limit the invention to the particular embodiments disclosed, but on the contrary, the intention is to cover all modifications, equivalents, and alternatives falling within the scope of the invention as defined by the appended claims.

BRIEF DESCRIPTION OF THE DRAWINGS

The preferred embodiments of the invention will be described in conjunction with the appended drawings provided to illustrate and not to limit the present invention, where like designations denote like elements, and in which.

DETAILED DESCRIPTION OF THE INVENTION

The invention relates a system and methods for medication therapy management to support improved adherence and alert clinicians of changes in behavior or symptoms. Advantageously, the system may improve adherence and facilitate patient engagement, care transition, and disease management, resulting in, for example, reduced healthcare costs for providers and payers, and enhanced drug use for pharmaceutical manufacturers, pharmacies, and specialty pharmacies.

Figure 1:
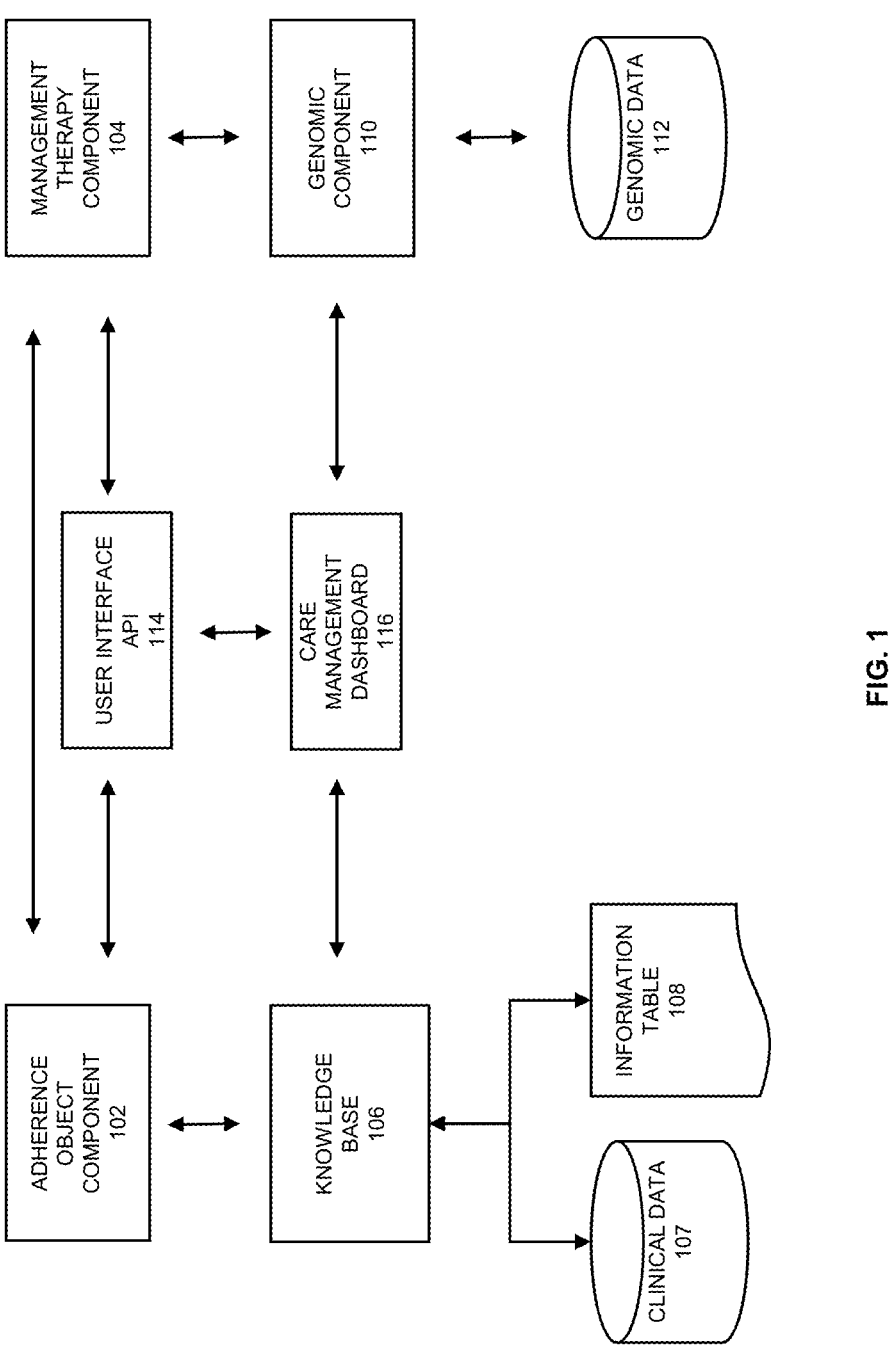
FIG. 1 illustrates an exemplary system that may be used to implement the methods according to the present invention.

Turning to the figures, FIG. 1 illustrates an exemplary system 100 for medication therapy management. As shown, system 100 may include an adherence object component 102 configured to interoperate with a management therapy component 104 and a knowledge base 106. While adherence object component 102, management component 104, and knowledge base 106 are shown as separate interoperating systems, it is contemplated that the functions of each respective component are subsystem components of a single integrated system.

Adherence object component 102 may be configured to uniquely differentiate the step by step intervention with a patient without involvement from a care delivery team. In particular, adherence object component 102 may prepopulate a therapy plan based on information accessible to the system to enable artificial intelligence and machine learning in a robust way. It is contemplated that adherence object component 102 may include and/or interact with a code generator to, for example, dynamically generate code to create events, drive next actions, and validate outcomes-based care. Adherence object component 102 may further include a model analyzer configured to process a model of the system to detect errors, perform optimization, and prepare for outputting the result.

Further, adherence object component 102 may be configured to manage workflow, execute rules, interface with external data, integrate with one or more EHRs, and more. In certain embodiments, adherence object component may integrate with an EHR via CDS Hooks and/or SMART-on- FHIR. It is further contemplated that adherence object component 102 may integrate with a genomic health record, as detailed below.

Management therapy component 104 be configured to facilitate providing patients with events, such as those generated by adherence object component 102. Events provided via management component 104 may include notifications directed to when, what, and how to take their medications.

Knowledge base 106 may be configured to provide access to information about a specific patient and/or a clinical topic stored in a clinical data archive 106 or information table 108. For example, knowledge base 106 may access one or more EHRs and retrieve information from various health care providers.

Knowledge base 106 may further be configured to retrieve genetic information (such as a patient's full genomic profile history), such as from a genomic component 110. Genomic system may be configured to access a database 112—such as a Genomic Archiving and Communication System—for display, review, and/or annotation of genomic information.

Also, knowledge base 106 may be configured to provide, for example, generalized information related to the medical condition and genomic information from various resources accessible to system 100. Examples of and sources accessible to knowledge base may include NCI Licensed treatments, NCCN, NCI PDQ, Clin Var, ClinGen, Pharm Var, CPIC, PharmGKB, Cravat, The Cancer Genome Atlas, NCI Genomic Data Commons, OncoKB, CIVIC, DGIdb, ClinicalTrials.gov.

Information accessible to system 100 may be stored in a format, such as Health Level-7 (HL7) or Fast Healthcare Interoperability Resources (FHIR) or translated into one of these formats before being stored and allocated within knowledge base by resource code and ICD code. This information may then be used to support the creation of a user interface, as detailed below. System 100 may also use the information to generate and display data entry forms, diagrams, or other user interface elements.

The interaction between adherence object component 102 and the knowledge base 106, and that which results from that interaction may be facilitated using a user interface applications program interface ("API") 114. User interface API 114 may facilitate the bi-directional association of clinical and genomic data and the related information accessed via knowledge base 106 with medication management and adherence information from adherence object component 102.

A user interface of system 100 may display a care management dashboard 200 for a patient. As shown in FIGS. 2-7, care management dashboard 200 may include descriptive components, graphical components, and temporal elements relating to, for example, medication therapy and adherence. Components of care management dashboard 200 may include interactive element that may be selected to obtain additional information, either specific to the patient or non-personalized reference information from a database, such as an adaptive data management database.

Figure 2:
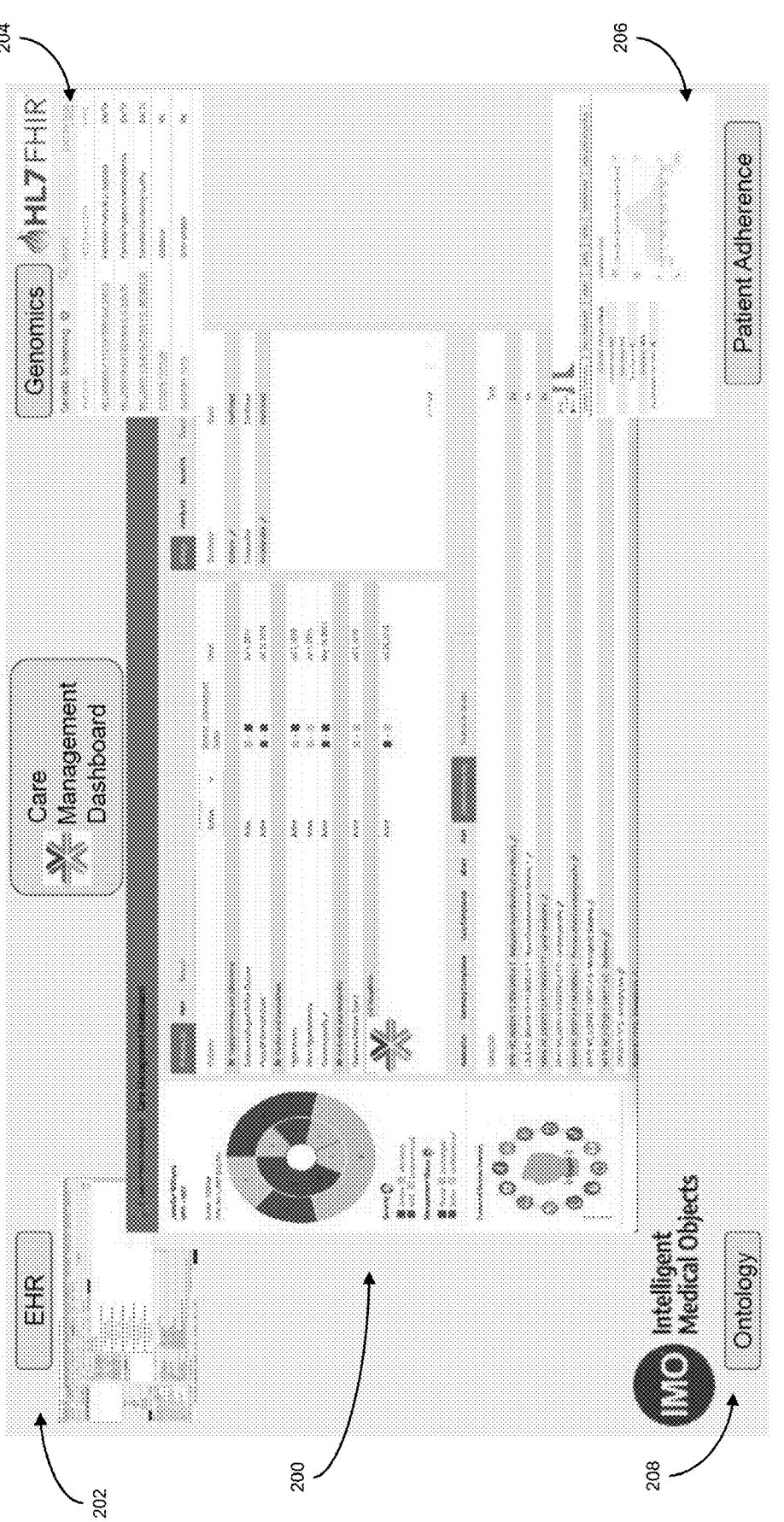
FIG. 2 illustrates an exemplary care management dashboard.

As shown in FIG. 2, dashboard 200 may be configured to access and interact with various components including, but not limited to, an electronic health record (EHR) 202, a genomics database 204, a patient adherence component 206, and an ontology component 208. Further, dashboard 200 may consists of multiple aspects going to the EHR 202, bringing the so-called fundamental variables that are important for longitudinal care modeling, such as medications (RX), diagnosis (DX), TX, history (HX). For purposes of care management, the patient history is often the most important element. The system further is configured to convert free text to a normalized dictionary. Through use of ontology component 208, the system may codify information, both from the diagnostics area, from the treatment area and from medications area, such that information may be aggregated and compared efficiently and effectively.

Figure 3:
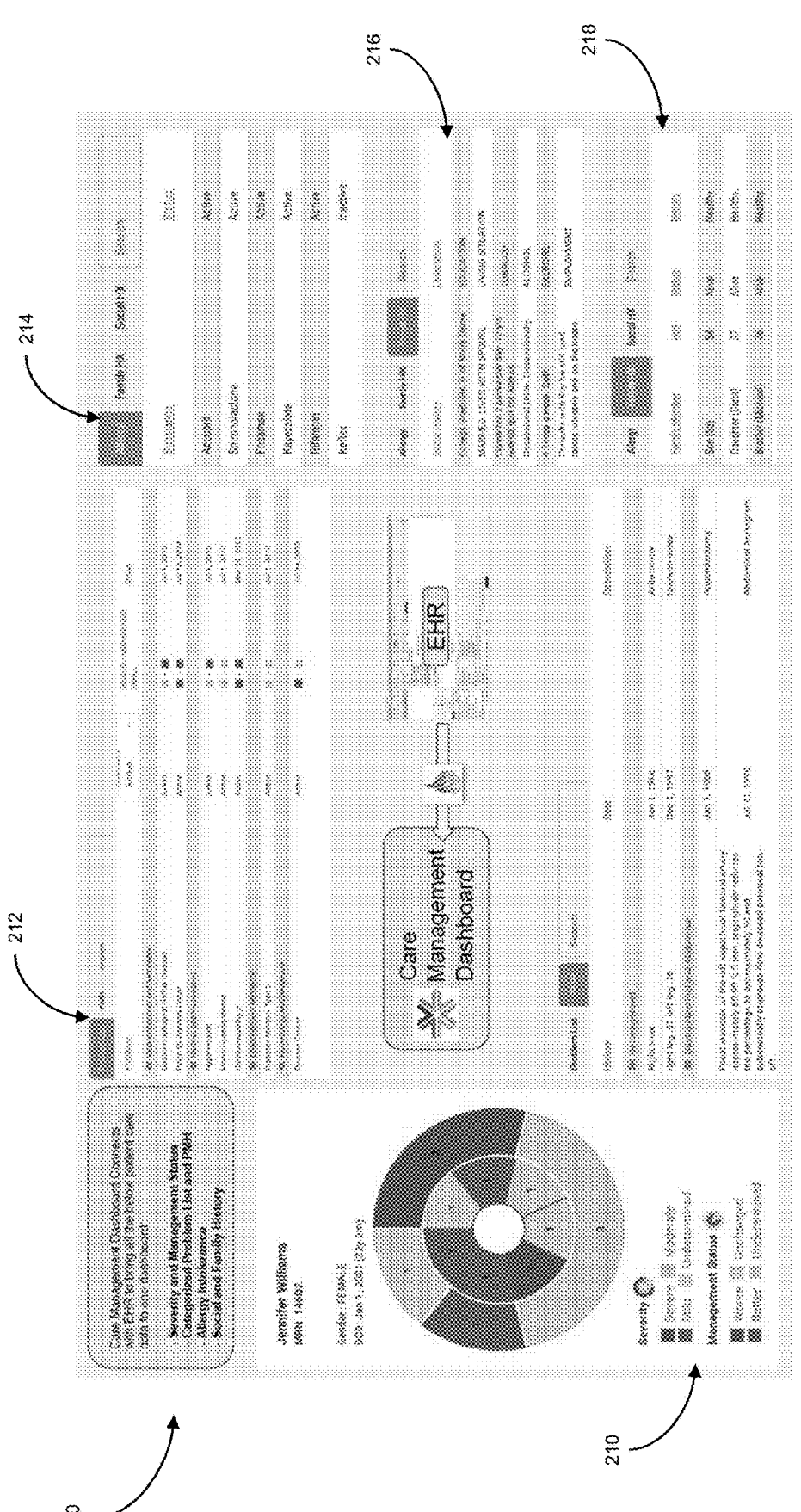
FIG. 3 illustrates an exemplary interaction between a care management dashboard may and electronic health record for presenting patient care information.

FIG. 3 illustrate an exemplary interaction between dashboard 200 may and EHR 202 for presenting patient care information. For instance, dashboard 200 may output patient data relating to severity and management status 210, categorized problems lists and past medical history 212, allergy intolerance 214, and social and family history 216, 218. Further the system may utilize an integrated electronic health record called IEMR, which is a problem-solving engine. Each problem has associated with the severity of the problem and associated with each treatment, and there is a status and severity combinations that identifies is this problem severe or is this problem is being managed correctly and the journey of the management.

Figure 4:
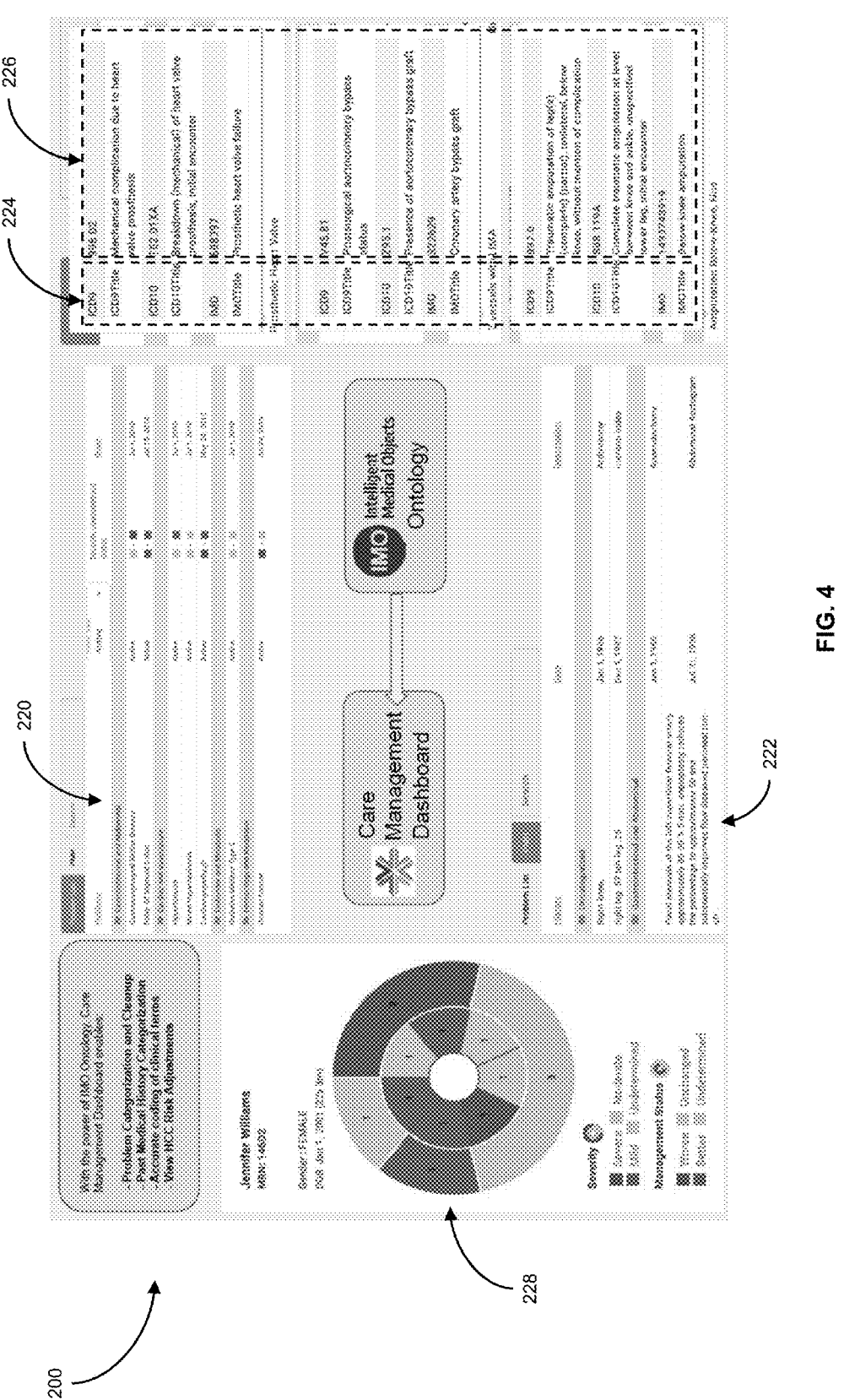
FIG. 4 illustrates an exemplary output of the care management dashboard including a visual representation of a patient status.

Further, as shown in FIG. 4, through use of knowledge base 104, care management dashboard 200 may enable problem categorization and cleanup 220, past medical history categorization 222, accurate coding of clinical terms 224, and views of hierarchical condition category risk adjustments 226. As illustrated, a visualization vehicle 228, such as the wheel may be used demonstrate the status of the care of the patient as analyze of the data.

Also, the visualization 228 may include coloring schemas that dynamically updated and thereby, for example, provide appropriate alerting to providers to care for the patients. For example, a coloring schema may represent a problems status identified as active, not active or resolved. Further, coloring schema may represent the severity associated with the management or status. In other words, how severe the problem is may be represented by a first color and the status and management of that problem may be represented by a second color. For instance, red in a status part may represent that the management is not working. Alternatively, a green color may represent that that the patient is stable. It is further contemplated that the system may take advantage of HL7 FHIR to bring the right data from the clinical system and from ancillary system 242 (FIG. 7) into dashboard 200.

Figure 5:
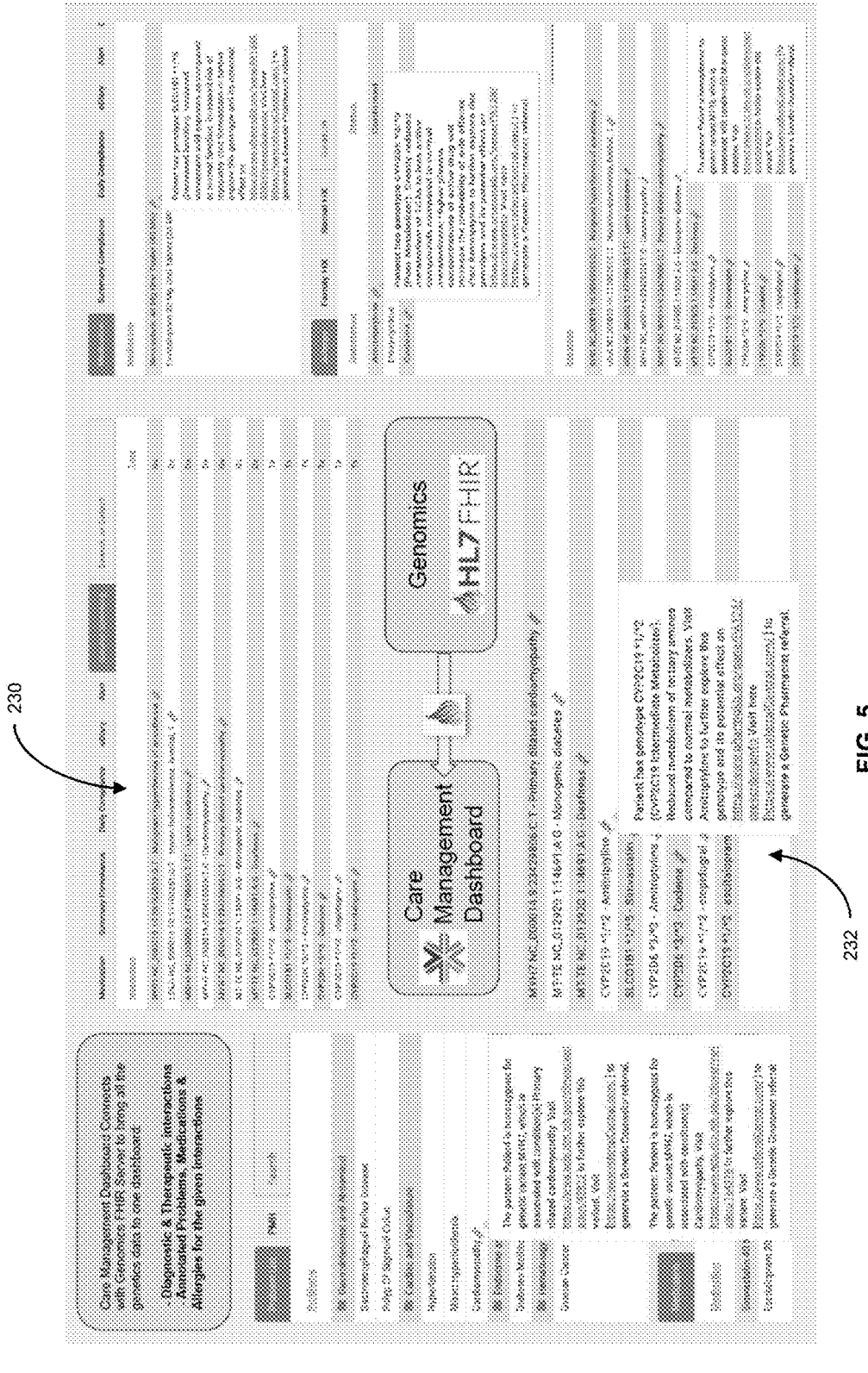
FIG. 5 illustrates an exemplary interaction between a care management dashboard may and genomic server.

As shown in FIG. 5, system 100 may further access and output genomic information via genomic component 106, such as a genomics FHIR server. Further, dashboard 200 may be configured to output and analyze genetic data 230 and explain genetic discoveries 232 to providers caring for patients. In other words, by expanding the repository, not only with making a repository a patient centric and adding value to it, but also obtaining the genetics at the point of care and attaching the genetic result to not only to the problem or diagnosis, also to the allergies and histories as well as to medications and treatment.

More specifically, through use of dashboard 200, system 100 may be configured to provide diagnostic and therapeutic interaction, annotated problems, and medications and allergies associated with a given interaction. When data is input into dashboard 200, the system is configured to normalize terminology and ontology. As a result, the system prevents duplicate problems being presented for patients with a comorbidity. It is contemplated that the medication or treatment that patient is on may have interactions and those interactions may be interacting with a different product. Further, by using normalized ontology, the system may group the diseases correctly to close classifications of the group and a concept within the clinical concepts.

Figure 6:
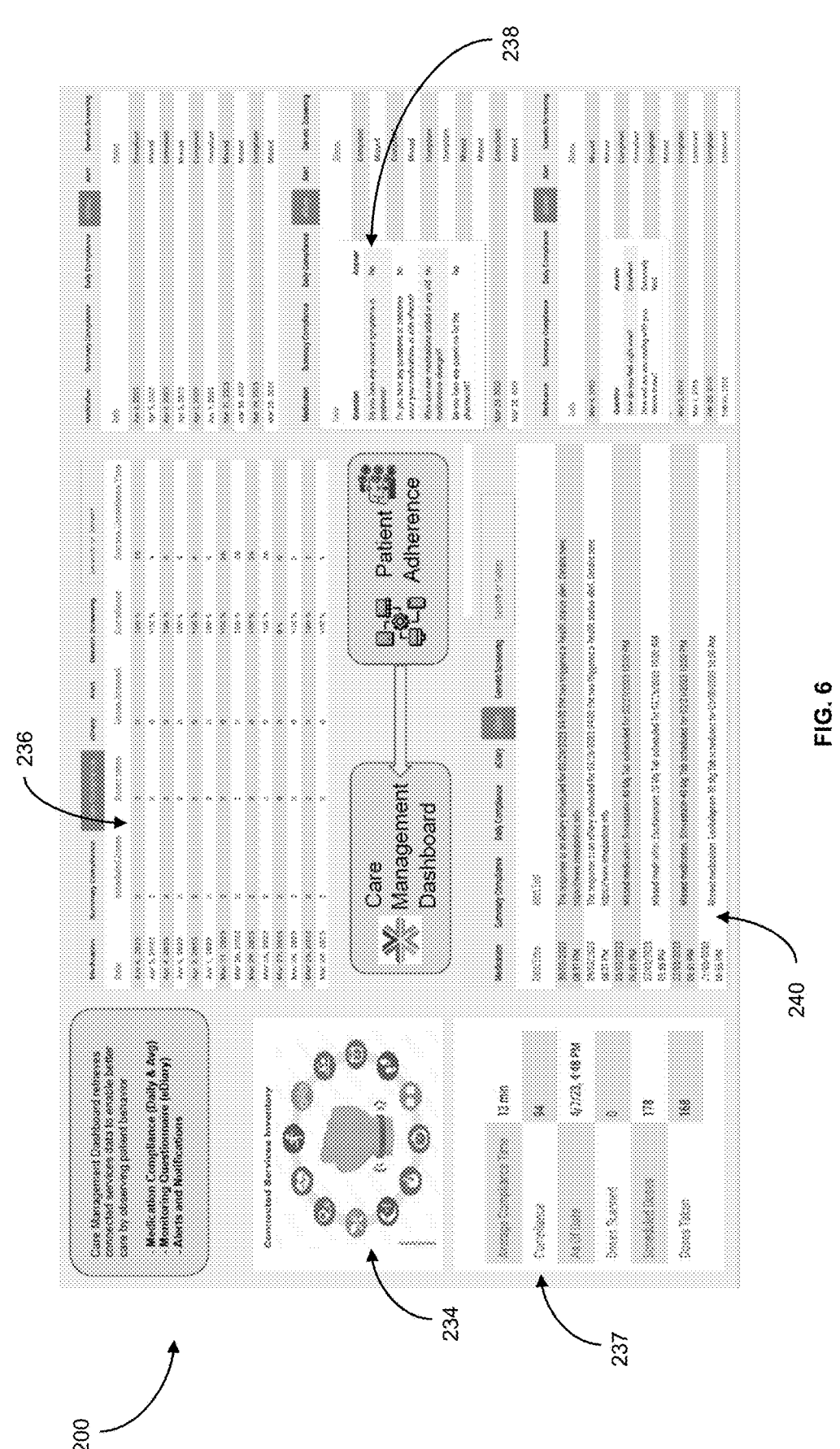
FIG. 6 illustrates an exemplary output of the care management dashboard including information accessible to the system via one or more connected devices.

Further, as shown in FIG. 6, system 100 may be configured to retrieve connected services data to, for example, provide for better care by observing patient behavior. Examples of data system 100 may receive from one or more connected devices 234 may include information relating to a patient's diet, sleep, exercise, and the like. This information may be output via dashboard 200 to monitor and display medication compliance 236, 237 questionnaires 238, and alerts and notifications 240.

For example, if the patient has an Apple Watch, the system may collect data associated with the patient's activities. The collected data may be used by the system for delivery of the code that is going to gather data. It is contemplated that when the order goes out, that order automatically generates code to correct and to gather data, especially during the patient reported outcome. Patient reported outcome could be a patient saying something, could be a watch saying something, could be blood glucose saying something, could be a weight saying something. Any data that gets collected from the environment that patient is involved in becomes patient reported outcome. That data then can be analyzed based on algorithm which is basically treatment specific algorithm to trigger event for the providers so the providers can see it.

Care management dashboard 200 may further display descriptive components, such as descriptive drawings, callouts, and captions that depict or describe a genome, anatomical feature and/or pathology as an overlay or modification on user interface.

Care management dashboard 200 may further output a virtual representation. A virtual representation may include a diagram corresponding to, for example, a severity of a problem and/or a status of management of the problem. In another example, a virtual representation may include anatomical sketches or actual medical images (such as X-ray or MRI images) corresponding to the patient.

Embodiments of system may permit a user to interact with one or more interactive components of care management dashboard 200 to retrieve, display, or record information. For instance, in response to a user input, system may display a descriptive component including previously recorded clinical data about the patient's condition, including allowing for recording, editing, and storage of this information. Examples of inputs that the system can receive include mouse clicks, typed text, touch, gestures, utterances, gaze data, image data.

To facilitate the diagnosis and treatment of the patient, system 100 may access relevant bodies of information, such as Clinical Decision Support Guidelines and Acceptable Use Criteria. In certain embodiments, analysis of the relevant genomic data and clinical data may be performed wholly by a user, automatically, or a combination of both.

Furthermore, system 100 may conduct health topic searches, provide recommendations for patient care, provide hyperlinks to relevant products and resources, and the like. As should be apparent to one of ordinary skill in the art from the disclosure herein, other related services may also be provided.

Figure 7:
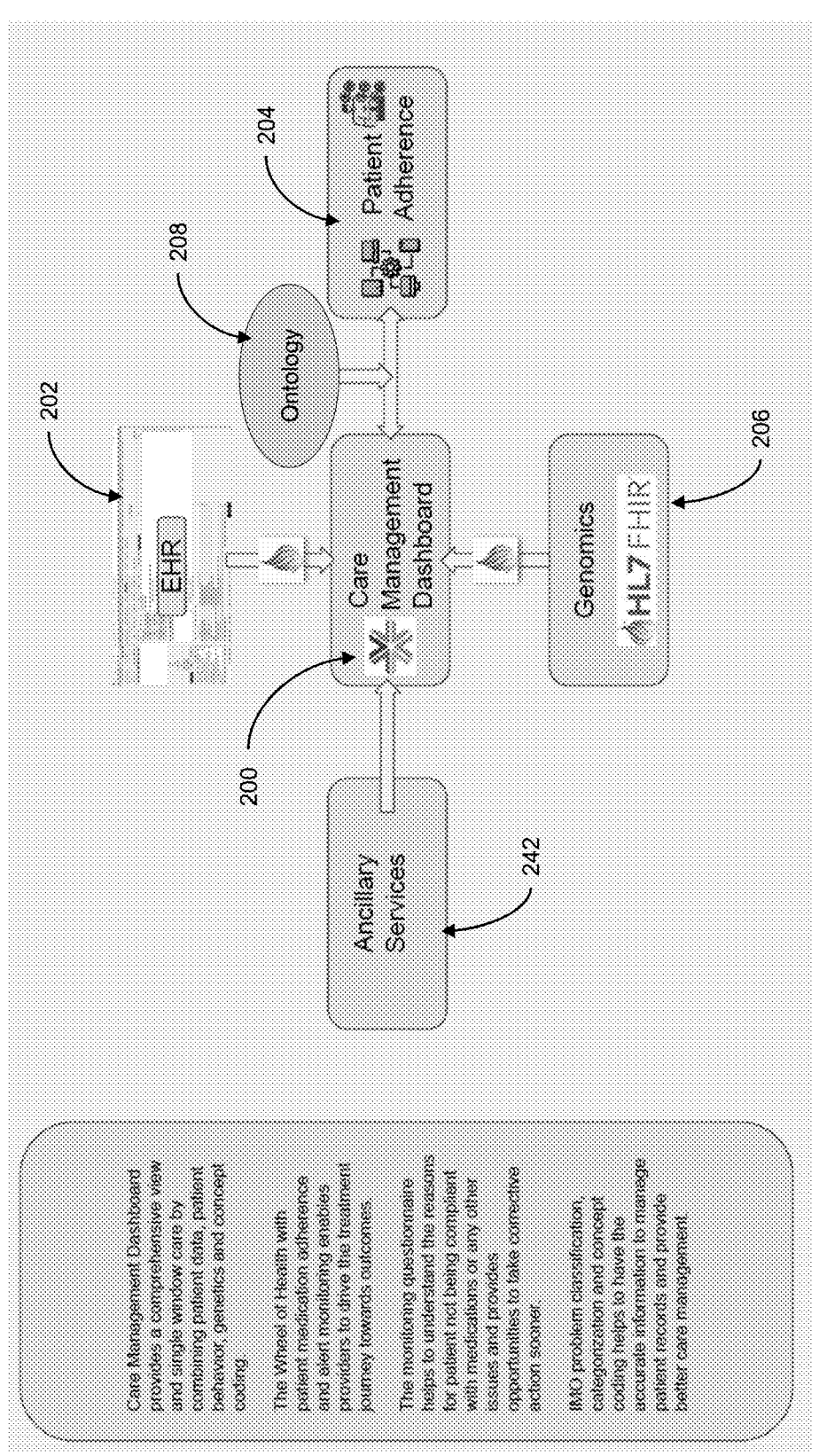
FIG. 7 illustrates a block diagram of components of the system that facilitate providing patient medication adherence and alert monitoring.

As shown in FIG. 7, by compiling long-term, longitudinal, clinical data 202 and genomic data 206 with information relating to adherence 206, patient behavior, and the like, care management dashboard 200 may be configured to provide a comprehensive view of patient-specific parameters at a point in time. As a result, system 100 may facilitate comparing patient parameters with those previously measured or with other individuals with similar profiles such that a medical professional may, for example, provide customized care management. Moreover, various components of dashboard

200 may provide patient medication adherence and alert monitoring to, for example, drive customized treatment plans.

Further, the monitoring of questionnaires output by system 100 may facilitate understanding reasons for non-compliance or other issues and provide for proactive interventions. Such interactions may be stored and properly managed by system 100 to provide for better care management.

Medication Therapy Management Component

As mentioned above, system 100 may include a medication therapy management (MTM) component, such as component 104 (FIG. 1). Users of a MTM component may include healthcare professionals (e.g. case managers, discharge planners, clinicians, physicians, and pharmacists) and patients (e.g. chronic disease, cancer, transplant, heart failure, assisted living). The level of access to the system's functionality and data views are varied and controlled through protocols implemented through an MTM interface or application by the systems administrator. These users can generally be described as either clinicians or patients.

The MTM application of the system may be configured to:

Set Patient preferences, such as lifestyle times (awake, sleep, breakfast, lunch, dinner), ring tones, message detail, name, language;

Call patient at scheduled times for medication events;

Call patient at scheduled times for scheduled events;

Provide information on when, why, and how to take a medication;

Provide scheduled questions to monitor symptoms, side effects, wellbeing, etc.;

Provide patient data on scheduled medications;

Contact doctor, caregiver, and tech-support;

Provide medication compliance history;

Provide diagnostic history relative to prescribed medications;

View upcoming scheduled events;

Scan to determine what is in medication container (for informational purposes); and Perform Offline Operation.

The MTM application may be output as an interactive application via an interface, such as a graphical user interface. Further, MTM application may be configured to generate events that facilitate providing auditory and textual notifications directed to when, what, and how to take their medications. Generated events may also be configured to verify and track the patient's symptoms and general health.

The events may include patient identification to verify the user. For instance, the application may output a message to confirm the identity of the patient. If the system is not able to verify the patient, the system may wait a period of time and present the message again. If the patient is verified, the application may output the event, such as the scheduled time to take a specific medication.

The application may also display additional inquiries and information, such as generalized or patient specific information. Additional inquiries output by the system may be in any form, such as multiple choice and free text input. Examples of additional inquiries may relate to the patient's adherence, type of medication, amount of medication remaining, changes to behavior, dosage or doctor, and the like. It is also contemplated that the system may require a visual confirmation to determine whether patient is taking the proper medication. For example, in response to receiving an image, the system may compare the uploaded image to a stored image-such as an image stored in knowledge base— to determine whether patient is taking the proper medication. Further, examples of additional information that the system may output may include generalized information related to the medication, such as prescription name, dosage, and instructions, desired results, potential side effects, refills remaining, and the like.

Adherence Object Component

System 100 may further include an adherence object component, such as component 102 (FIG. 1), configured to interact with the medication therapy management application. In particular, adherence object component (AO) may be configured to automate the collection of adherence and outcomes data with every physician order.

The AO component may be a stateless application that becomes a platform for therapy plannings tools. The AO component may prepopulate a therapy plan based on, for example, a time order to enable artificial intelligence and machine learning in a robust way. For instance, system 100 may dynamically generate code at the time of order to create events, drive next actions, and validate outcomes-based care, as detailed below. In one example, through use of system 100, a therapy plan (e.g., treatment, order, and the like) may be prepared by the clinician and placed in a blockchain to protect the clinical information and preserve clinical intent, creating a marketplace for treatment modality.

The AO component may reside in a meta-layer of an application. The application platform may be deployed to both enterprise solutions and personal health platforms through, for example, an HL7 HAPI-FHIR interface. Platform components may include a source (outside integration point such as an EHR or PHR), adherence engine with events module (from connected devices), and reporting and alerting services.

Through use of a HAPI-FHIR interface, system 100 may be configured to compare actual adherence to the therapy plan. Based on this comparison, system 101 may be configured to determine the compliance state of an adherence object through use of predetermined and/or dynamically adjusted that are patient and schedule-specific. It is further contemplated that system 100 may be configured to track the transition of the adherence object states (e.g., from compliant to noncompliant), handle the various adherence states, and detect events upon transition for alerting a user, thereby creating a timeline of events based on the health record.

In one aspect of system 100, the AO component may include an adherence engine and an object element. The adherence engine may be configured to align or associate a clinician-authored treatment plan (i.e., expected behavior) with patient data (i.e., actual behavior) based on, for example, a disease, disease state, and corresponding longitudinal data. The alignment of treatment plans with patient data may increase the potential for medication and treatment adherence, ideally leading to improved care outcomes and patient retention. Patient adherence may then be monitored based on expected treatment plan behavior as compared to actual patient behavior to predict outcomes.

An object element of the AO component may correspond to the data and logic dedicated to that clinician-patient treatment plan that supports EMR and patient-platform integration via standard interfaces. Object element may be configured to collect and interpret data associated with patient adherence. The collected information may be leveraged for analytical purposes. Analytics may be applied in real-time, prospectively or retrospectively, per patient and/or across patient cohorts based on inclusion and exclusion criteria. Further, alerts may be customized and provided directly to clinicians and patients to support improved adherence and to alert clinicians of changes in behavior or symptoms.

Code Generation

As mentioned above, a component of the system may dynamically generate or retrieve code to, for example, create events, drive next actions, and validate outcomes-based care. Code may be generated in any suitable programming language, such as Python, C#.NET, and the like. For instance, code may be generated based on the following:

Type of medication therapy will this system be used to schedule (e.g., oral medications, injections, infusions, etc.)?

Parameters that need to be taken into account when scheduling medication therapy (e.g., dosage, frequency, duration, time of day, etc.)?

Constraints or rules that need to be enforced when scheduling medication therapy (e.g., maximum dosages per day, minimum time intervals between doses, interactions with other medications, etc.)?

Format of the input data for the scheduling system (e.g., CSV file, database, web API, etc.)?

Expected output of the scheduling system (e.g., a list of scheduled medication doses, a calendar view of scheduled doses, etc.)?

Code generation may be used to identify the treatment, that treatment can then dynamically generate code for adherent objects. Further, that generation of the code may be tweaked based on the environment that patient is. The environment may be information obtained from the patient, a smartphone, and any other smart device that the system is capable of communication with.

Based on the code generated, the system may be configured to monitor day by day activity of the patient adherence, and the relationship between the patient with the treatment adherent to the patient condition. The treatment adherent to the patient condition may allow providers to stop the treatment immediately when they see a problem. Similar method may be applied for use with pre-surgical and post-surgical settings.

Exemplary Code

In one example, code may be automatically generated using for the AO that would use Python and the Kivy framework. The generated code may then be compared by ChatGPT to code generated by Bing. The method is shown below.

ChatGPT Request: Can you generate code to schedule simvastatin 20 mg tablet once a day in the evening on an empty stomach using Python and the Kivy framework for me?

Bing Request: Generate code to schedule simvastatin 20 mg tablet once a day in the evening on an empty stomach using Python and the Kivy framework

| ChatGPT Code | Bing Code |
|---|---|
| Certainly, here's some sample code in Python that uses the Kivy framework to create a basic GUI that allows the user to schedule a daily dose of simvastatin 20mg tablet in the evening on an empty stomach:<br><br>```import kivy\nfrom kivy.app import App\nfrom kivy.uix.boxlayout import BoxLayout\nfrom kivy.uix.label import Label\nfrom kivy.uix.button import Button\nclass MedicationSchedule(BoxLayout):\n    def __init__(self, kwargs):\n        super(MedicationSchedule, self).__init__(kwargs)\n        self.medication = "Simvastatin 20mg"\n        self.schedule = "Once a day in the evening on an empty stomach"\n        self.evening_time = "8:00 PM"\n        self.reminder_label = Label(text="")\n        # Create UI elements\n        medication_label = Label(text="Medication: " + self.medication)\n        schedule_label = Label(text="Schedule: " + self.schedule)\n        time_label = Label(text="Time: " + self.evening_time)\n        reminder_button = Button(text="Set Reminder", on_press=self.set_reminder)\n        # Add UI elements to layout\n        self.add_widget(medication_label)\n        self.add_widget(schedule_label)\n        self.add_widget(time_label)\n        self.add_widget(reminder_button)\n        self.add_widget(self.reminder_label)\n    def set_reminder(self, instance):\n        # Code to set a reminder at the designated time\n        # This could be implemented using a library like schedule or apscheduler``` | Sure! Here's a sample code that schedules simvastatin 20mg tablet once a day in the evening on an empty stomach using Python and the Kivy framework:<br><br>```from kivy.app import App\nfrom kivy.uix.label import Label\nfrom kivy.clock import Clock\nclass MedicationSchedule(App):\n    def build(self):\n        label = Label(text='Simvastatin 20mg tablet once a day in the evening on an empty stomach')\n        Clock.schedule_once(self.take_medication, 86400) #86400 seconds = 1 day\n        return label\n    def take_medication(self, dt):\n        print('Time to take medication')\nif __name__ == '__main__':\n    MedicationSchedule().run()``` |

-continued

| ChatGPT Code | Bing Code |
|---|---|

```
    # Here's some sample code using
apscheduler:
    from apscheduler.schedulers.background
import BackgroundScheduler
    from datetime import datetime
    def reminder( ):
        self.reminder_label.text = "Time to
take your " + self.medication + " dose for
today."
    scheduler = BackgroundScheduler( )
    scheduler.start( )
    scheduler.add_job(reminder, 'cron',
hour=20, minute=0) # Set reminder for 8:00
PM
```

This code creates a Kivy app that displays a label with the medication details and schedules a function called take_medication to run once every day (86400 seconds) using Kivy's Clock.schedule_once method1. You can modify this code to suit your needs.
I hope this helps! Let me know if you have any other questions.

A next step may involve performing a detailed analysis of ChatGPT producing Python and C#.NET code. The goal may be to evaluate source code that ChatGPT can generate for daily medication scheduling, which is a core of functionality for AO.

Original ChatGPT Prompt: Can you generate code to schedule medication therapy for me.

Original Python Code Generated from ChatGPT:

```
import datetime
# Define medication schedule
medication_schedule = [
    {'medication': 'Aspirin', 'dose': '81mg', 'route': 'Oral', 'schedule': 'daily', 'time':
datetime.time(hour=8, minute=0)},
    {'medication': 'Lisinopril', 'dose': '20mg', 'route': 'Oral', 'schedule': 'daily', 'time':
datetime.time(hour=12, minute=0)},
    {'medication': 'Metformin', 'dose': '500mg', 'route': 'Oral', 'schedule': 'twice daily', 'time':
datetime.time(hour=8, minute=0)},
    {'medication': 'Atorvastatin', 'dose': '10mg', 'route': 'Oral', 'schedule': 'daily', 'time':
datetime.time(hour=20, minute=0)}
]
# Define start date and end date
start_date = datetime.date.today( )
end_date = start_date + datetime.timedelta(days=30)
# Define function to generate medication schedule for a given date range
def generate_medication_schedule(start_date, end_date, medication_schedule):
    schedule = [ ]
    current_date = start_date
    while current_date <= end_date:
        for medication in medication_schedule:
            if medication['schedule'] == 'daily':
                medication_time = medication['time']
                medication_datetime = datetime.datetime.combine(current_date, medication_time)
                schedule.append({'medication': medication['medication'], 'dose': medication['dose'],
'route': medication['route'], 'datetime': medication_datetime})
            elif medication['schedule'] == 'twice daily':
                medication_time_1 = medication['time']
                medication_time_2 = medication['time'] + datetime.timedelta(hours=12)
                medication_datetime_1 = datetime.datetime.combine(current_date,
medication_time_1)
                medication_datetime_2 = datetime.datetime.combine(current_date,
medication_time_2)
                schedule.append({'medication': medication['medication'], 'dose': medication['dose'],
'route': medication['route'], 'datetime': medication_datetime_1})
                schedule.append({'medication': medication['medication'], 'dose': medication['dose'],
'route': medication['route'], 'datetime': medication_datetime_2})
        current_date += datetime.timedelta(days=1)
    return schedule
```

-continued

```
# Generate medication schedule for the given date range
schedule = generate_medication_schedule(start_date, end_date, medication_schedule)
# Print medication schedule
for medication in schedule:
    print(f" {medication['datetime'].strftime('%Y-%m-%d %H:%M:%S')}:
{medication['medication']} {medication['dose']} {medication['route']}")
```

Issues corrected to get the working code: Variable name [10] collisions; Global/Local scoping issues with variable names; General, minor readability issues.
Working Python Code:

```
import datetime
# Define medications and their respective time intervals
medication_schedule = [
    {'medication': 'Aspirin', 'dose': '81mg', 'route': 'Oral', 'schedule': 'daily',
        'time': datetime.time(hour=8, minute=0)},
    {'medication': 'Lisinopril', 'dose': '20mg', 'route': 'Oral', 'schedule': 'daily',
        'time': datetime.time(hour=12, minute=0)},
    {'medication': 'Metformin', 'dose': '500mg', 'route': 'Oral', 'schedule': 'twice daily',
        'time': datetime.time(hour=8, minute=0)},
    {'medication': 'Atorvastatin', 'dose': '10mg', 'route': 'Oral', 'schedule': 'daily',
        'time': datetime.time(hour=20, minute=0)}
]
# Create an empty array to hold all the scheduled med events when calculated
schedule = [ ]
# Define function to generate medication schedule for a given date range
def generate_medication_schedule(start_date_p, end_date_p, medication_schedule_p):
    """"Generate medication schedule for a given date range."""
    current_date = start_date
    twice_daily_interval = datetime.timedelta(hours=12)
    # Schedule from current date to end date
    while current_date <= end_date:
        # Process for each medication
        for med in medication_schedule:
            if med['schedule'] == 'daily':
                # Get the time interval for this med
                medication_time = med['time']
                # Calc the time for the med event
                medication_datetime = datetime.datetime.combine(current_date, medication_time)
                # Append the record to the schedule
                schedule.append(
                    {'medication': med['medication'], 'dose': med['dose'], 'route': med['route'],
                        'datetime': medication_datetime})
            elif med['schedule'] == 'twice daily':
                # Get the time interval for this med
                medication_time = med['time']
                # Create 2 times for twice-daily meds
                medication_datetime_1 = datetime.datetime.combine(current_date, medication_time)
                medication_datetime_2 = medication_datetime_1 + twice_daily_interval
                # Append the 1st first of 2 daily scheduled med events for this med to the schedule
                schedule.append(
                    {'medication': med['medication'], 'dose': med['dose'], 'route': med['route'],
                        'datetime': medication_datetime_1})
                # Append the 2nd of 2 daily scheduled med events for this med to the schedule
                schedule.append(
                    {'medication': med['medication'], 'dose': med['dose'], 'route': med['route'],
                        'datetime': medication_datetime_2})
        # Now go to the next day and repeat the scheduling
        current_date += datetime.timedelta(days=1)
    # Return the schedule, sorted by datetime in the
    return sorted(schedule, key=lambda x: x['datetime'])
# Press the green button in the gutter to run the script.
If_name_ == '_main_':
    # Define start date and end date for the schedule
    start_date = datetime.date.today( )
    end_date = start_date + datetime.timedelta(days=30)
    # Generate medication schedule for the given date range
    schedule = generate_medication_schedule(start_date, end_date, medication_schedule)
    # Print medication schedule
    for medication in schedule:
        print(
            f" {medication['datetime'].strftime('%Y-%m-%d %H:%M:%S')}:
{medication['medication']} {medication['dose']} {medication['route']}")
```

Original ChatGPT Prompt for the same output but in the C#.NET programming language: Can you generate C#.NET code to schedule medication therapy for me Original Response from ChatGPT: Certainly! However, I will need more information about the requirements of the medication therapy scheduling system before generating code. Could you please provide me with some additional details, such as:

1. What types of medication therapy will this system be used to schedule (e.g., oral medications, injections, infusions, etc.)?
2. What are the parameters that need to be taken into account when scheduling medication therapy (e.g., dosage, frequency, duration, time of day, etc.)?
3. Are there any constraints or rules that need to be enforced when scheduling medication therapy (e.g., maximum dosages per day, minimum time intervals between doses, interactions with other medications, etc.)?

4. What is the format of the input data for the scheduling system (e.g., CSV file, database, web API, etc.)?
5. What is the expected output of the scheduling system (e.g., a list of scheduled medication doses, a calendar view of scheduled doses, etc.)?

Once I have more information, I can generate C#.NET code to implement the medication therapy scheduling system.

Response to ChatGPT: The route of medications can be any: oral, injectable, etc. Daily Dosage and Frequency, no constraints or rules, just scheduling each medication event. No input format, you can define your own test data in the program. Expected output is a list of dates/times for all scheduled medication events.

Original Response and C#.NET Code Generated from ChatGPT: Thank you for providing additional details about the medication therapy scheduling system. Here is some C#.NET code that implements the system:

```
using System;
using System.Collections.Generic;
class MedicationEvent
{
    public string MedicationName { get; set; }
    public string Route { get; set; }
    public int Dosage { get; set; }
    public TimeSpan Frequency { get; set; }
    public DateTime StartTime { get; set; }
    public DateTime EndTime { get; set; }
    public List<DateTime> GetScheduledTimes( )
    {
        var scheduledTimes = new List<DateTime>( );
        var currentTime = StartTime;
        while (currentTime < EndTime)
        {
            scheduledTimes.Add(currentTime);
            currentTime = currentTime.Add(Frequency);
        }
        return scheduledTimes;
    }
}
class Program
{
    static void Main(string[ ] args)
    {
        var medicationEvents = new List<MedicationEvent>( );
        // Define test medication events
        medicationEvents.Add(new MedicationEvent
        {
            MedicationName = "Ibuprofen",
            Route = "Oral",
            Dosage = 200,
            Frequency = TimeSpan.FromHours(8),
            StartTime = new DateTime(2023, 3, 19, 8, 0, 0),
            EndTime = new DateTime(2023, 3, 22, 0, 0, 0)
        });
        medicationEvents.Add(new MedicationEvent
        {
            MedicationName = "Insulin",
            Route = "Injectable",
            Dosage = 10,
            Frequency = TimeSpan.FromHours(12),
            StartTime = new DateTime(2023, 3, 19, 8, 0, 0),
            EndTime = new DateTime(2023, 3, 21, 0, 0, 0)
        });
        // Generate list of scheduled times for each medication event
        foreach (var medicationEvent in medicationEvents)
        {
            var scheduledTimes = medicationEvent.GetScheduledTimes( );
            Console.WriteLine("Medication: " + medicationEvent.MedicationName);
            Console.WriteLine("Route: " + medicationEvent.Route);
            Console.WriteLine("Dosage: " + medicationEvent.Dosage + "mg");
```

-continued

```
        Console.WriteLine("Frequency: " + medicationEvent.Frequency.TotalHours + " hours");
        Console.WriteLine("Scheduled times:");
        foreach (var scheduledTime in scheduledTimes)
        {
            Console.WriteLine(scheduledTime);
        }
        Console.WriteLine( );
    }
  }
}
```

Issues: Some minor organizational issues with regards to code segments; Generates code for a schedule for each medication individually rather than an overall daily schedule [15] incorporating all medications. Again, a minor issue and easily corrected.

Working C#.NET Code:

```
using System;
using System.Collections.Generic;
namespace MedSchedulingFromChatGPT
{
    class MedicationEvent
    {
        public string MedicationName { get; set; }
        public string Route { get; set; }
        public int Dosage { get; set; }
        public TimeSpan Frequency { get; set; }
        public DateTime StartTime { get; set; }
        public DateTime EndTime { get; set; }
        public List<DateTime> GetScheduledTimes( )
        {
            var scheduledTimes = new List<DateTime>( );
            var currentTime = StartTime;
            while (currentTime < EndTime)
            {
                scheduledTimes.Add(currentTime);
                currentTime = currentTime.Add(Frequency);
            }
            return scheduledTimes;
        }
    }
    class Program
    {
        static void Main(string[ ] args)
        {
            var medicationEvents = new List<MedicationEvent>( );
            // Define test medication events
            medicationEvents.Add(new MedicationEvent
            {
                MedicationName = "Ibuprofen",
                Route = "Oral",
                Dosage = 200,
                Frequency = TimeSpan.FromHours(8),
                StartTime = new DateTime(2023, 3, 19, 8, 0, 0),
                EndTime = new DateTime(2023, 3, 31, 0, 0, 0)
            });
            medicationEvents.Add(new MedicationEvent
            {
                MedicationName = "Insulin",
                Route = "Injectable",
                Dosage = 10,
                Frequency = TimeSpan.FromHours(12),
                StartTime = new DateTime(2023, 3, 19, 8, 0, 0),
                EndTime = new DateTime(2023, 3, 31, 0, 0, 0)
            });
            // Generate list of scheduled times for each medication event
            foreach (var medicationEvent in medicationEvents)
            {
                var scheduledTimes = medicationEvent.GetScheduledTimes( );
                Console.WriteLine("Medication: " + medicationEvent.MedicationName);
                Console.WriteLine("Route: " + medicationEvent.Route);
                Console.WriteLine("Dosage: " + medicationEvent.Dosage + "mg");
                Console.WriteLine("Frequency: " + medicationEvent.Frequency.TotalHours + "
hours");
```

-continued

```
    Console.WriteLine("Scheduled times:");
    foreach (var scheduledTime in scheduledTimes)
    {
        Console.WriteLine(scheduledTime);
    }
        Console.WriteLine( );
    }
    Console.ReadKey( );
    }
}
```

Exemplary Steps and Patient States

The AO may be initiated by a treatment order from a provider. Each order may have designated protocols to be followed (e.g., "two pills twice a day with meals"), based on observed facts, and connected to the diagnosed problem. Specifically, the system may be configured to link the order to the patient problem list in order for the AO to deliver an optimal value in measuring treatment adherence.

Medication orders may require a physician's order, pharmacy approval and/or dispensing to the patient. Exemplary information that a pharmacy may need for each medication may include:

Name of the prescriber;

Names of medications prescribed;

Start date for the medication;

Medication schedule for the day;

Awake, Breakfast, Lunch, Evening, Dinner, Sleep, or custom (e.g., number of times per day);

The number of days the medication needs to be taken; and

Smart-on-FHIR Facesheet for patient's medical information.

When an order is finalized, a list of scheduled medication events may be generated for each medication that describes the therapy plan organized by time. This scheduled medication events list may be used to monitor the transition between the AO states. With the AO component, the system may schedule and manage adherence states on a user device, which may include an operating system configured to act as a communication vehicle to keep the treating prescriber and patient electronic medical record updated with the patient's adherence to the treatment schedule as defined by the prescriber.

Figure 8:
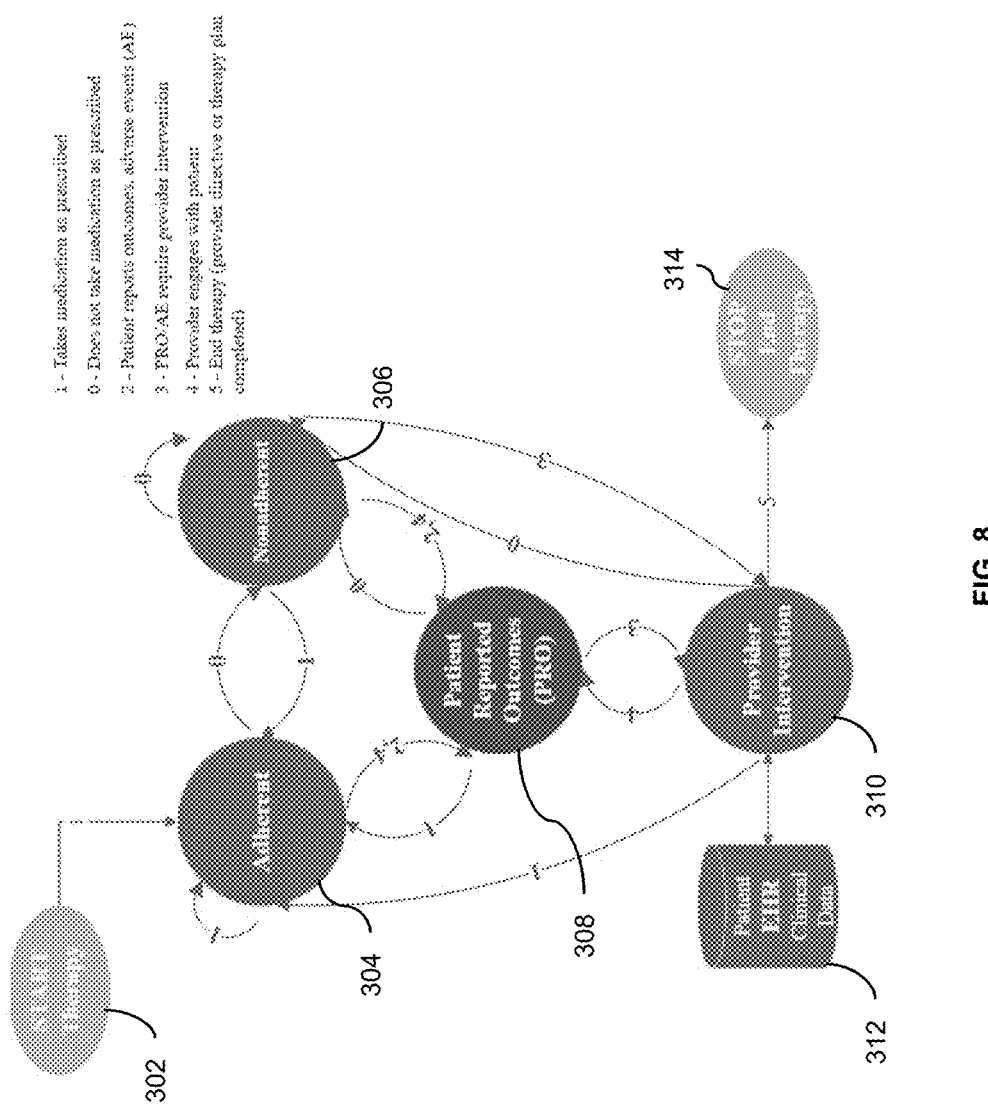
FIG. 8 illustrates an exemplary flowchart corresponding to exemplary adherence states of a patient.

FIG. 8 illustrates a flowchart 300 corresponding to exemplary states of a patient. As shown, a therapy management process may begin 302 (e.g., a medication is prescribed to a patient) and, depending on the patient's adherence, system 100 may determine a state of the patient, such as "adherent" 304, "non-adherent" 306, "patient adverse event" 308, "provider intervention" 310, "additional analysis request" 312, and "end of treatment" 314.

In the use case describing adherence to medication therapy, the time and date for each dosing event may be key variables used to monitor adherence. The AO cycle may begin when the first notification for the dosing event is sent based on the physician order. When the patient receives the dosing event notification and responds affirmatively that the medication was taken (AOR=Y=1), the patient will be in the "Adherent" state. Any past dosing event notifications for which the patient did not respond will be marked as non-adherent (AOR=N=0). It is also contemplated that, through use of the AO component, a patent may be presented with one or more options and manually input their adherence state for the selected period.

An adherent state may be detected by the AO component. In response, system 100 may facilitate generating an entry in an output table corresponding to the patient's adherence at the prescribed period, e.g., date and time. A non-adherent state may be detected by the AO component when, for example, the patient does not respond to the dosing event notification within the grace period. Moreover, the non-adherent state may correspond to a patient confirming that the medication was not taken as prescribed. In response, the AO component may be configured to mark the dosing event notification as nonadherent (AOR=N=0) and update a record to reflect the non-adherent state of the patient.

A patient adverse event and/or provider intervention state may be trigged by various parameters. For instance, techniques that the system may implement used to determine an adverse event may include direct text, speech to text, NLP with token extraction, token with clinical coding, and pattern matching. A provider intervention state may be triggered in response to an adverse event that the system determines requires intervention. It is further contemplated that the intervention state may be triggered in response to determining that the patient is non-adherent or has failed to report adherence for a given number of events, which may be established in, for example, a medication order or defined by a set of rules.

Another state of the AO component may include a request for additional data analysis. The system provides for at least one point of interaction between the patient and provider. During this interaction, a provider may request additional information for relating to, for example, the patient, a medical order, behavior, symptoms, and the like. The provider request may also include information from an EHR accessible to the system.

The system may further detect an end of treatment state. If system 100 determines that that there is no further event (e.g., dosage events) notification associated with an order or medication, an end of treatment state may be triggered. Moreover, the end of treatment state may be determined during a provider intervention. For instance, system 100, in response to an input, may determine that the current treatment should end based on, for example, non-adherence or an adverse event.

Adaptive Data Management (ADM) Component

One or more components of system 100 may interact with an adaptive data management (ADM) model (not shown). An ADM may be a static database model provided and optimized for manipulation of large volumes of data with a standard front-end component interface, thereby simplifying database design and data access, while reducing development cost and development time. Furthermore, the model does not require numerous qualified technical personnel to monitor all database activity, the data to be collected is described, both in format and in relationships, as meta data to the model, and user data (instance data) is then collected and stored using the format defined by the meta data. In tests, the inventive method and system have shown success in managing large numbers of records and in document indexing as useful in such applications as web sites. Due to the nature of ADM data storage, the data requires little of no cleansing before inclusion into a data warehousing database.

ADM provides access protection and tracking, ensuring data security and integrity, through a gateway requiring identity authentication and multi-layered access control. ADM manages multiuser access and concurrency.

The ADM may be used with an Oracle database running on any of several platforms to provide the data storage support, with as many as about 14 or more objects participating to the design. A set of components, developed as Microsoft COM objects, provide access to user front-end applications.

ADM may provide both a back-end information storage infrastructure and a flexible development environment for data storage. ADM may be based on a meta data model. The organization of the data itself (the meta data) is described to ADM prior to any collection of data. The meta data model encloses definitions of meta data elements as well as the relationships among these meta data elements. Data elements may be organized as trees, i.e., a meta data element has at most one parent data element, or as graphs, i.e., a meta data element may have one or more parent data elements, thus allowing representations of most possible data models.

ADM may provide support for multiple development environments, using a simple component interface for complex back-end data storage, thereby simplifying access to instance data. Instance data consists of stored user data patterned after the meta data definition. The development environment includes a COM object, accessed from all applications referencing ADM, and an administration tool for model management. ADM allows transfer of data to and from ADM using XML. The XML document type definition is defined by the meta data definition.

ADM may facilitate accessing to conventional development environments (Microsoft Visual C++ and Visual Basic, Borland Delphi) as well as web environment tools such as Microsoft Active Server Pages (ASP). This tool is well suited for short transactions characteristic of web environments.

ADM may provide additional simplified data access to any user, from the relational database manager standpoint, by allowing view definitions. A view consists of many meta data elements, which may be tightly or loosely connected. As instance data is created, any user can access the instance data represented as views, from any database environment tools, such as Microsoft Access or Microsoft MS Query.

ADM may be complemented by Visual ADM. ADM and Visual ADM may fit to the object-oriented document-view paradigm, such as: ADM provides the data back end (document layer), while Visual ADM provides user interface(s) to the user (visual layer). Visual ADM may be a thin-client form-based application: forms are defined as scripts, stored into the ADM database, and retrieved at the Visual ADM client location when requested. Visual ADM also provides a robust scripting language, allowing forms to implement any type of business rules.

ADM and Visual ADM may be provided in the form of an InstallShield application, including an ADM COM object, ADM Administration Tool, two Visual ADM executables, several PDF documents ('ADM User Manual', 'ADM Administration Tool User manual', 'Visual ADM User Manual', 'Visual ADM Reference Manual'), as well as a sample implementation. In one embodiment of the invention, a running instance of Oracle8i is required prior to installation.

It is further contemplated that components of ADM may facilitate using both graph and tree structures in an optimized data model stored in a relational database. Also, ADM permits presentation of stored data as conventional tables (data view) for standard reporting. As the data changes and expands, the content of the data views reflects the changes. Any of these data views can be defined by end users and created automatically by ADM back end service. ADM provides a component for simple front-end interface development using Microsoft COM objects while providing access to each aspect of the inventive method and system. Moreover, ADM provides a transactional data access model suitable for web-based and client-server implementation.

Longitudinal Electronic Medical Record

System 100 may further interact with a longitudinal electronical medical record (LEMR). The LEMR may include a record of patient health information generated by one or more encounters in any care delivery setting, by one or more care providers. Included in this information may be patient demographics, chief complaints, physical exams, review of systems, progress notes, problems, medications, plans, vital signs, history information (including past medical, surgical, medication, test, social, travel, immunization, obstetric, growth chart and developmental history), laboratory data, subjective, objective, assessment and plan (SOAP) notes, radiology reports, genetic information, scanned documents, referral documents, as well as other information commonly known in the art.

The LEMR may be configured to automate and streamline the clinician's workflow. It may have the ability to generate a complete record of a clinical patient encounter, as well as to support other care-related activities directly or indirectly including evidence-based decision support, quality management, and outcomes reporting.

An aspect of the LEMR may facilitate showing show data element continuity and the relationships between elements generated in multiple instances, in other words, show a patient data point over time, and also show this data point in relation to other data points. Furthermore, an element should be considered polymorphic. For example, while element X may first be identified as a chief complaint, element X may be later elevated to a patient problem and then later be considered past medical history. An element first identified as a plan may be updated or modified. An element initially declared as a medication may be retired, thus becoming medication history. Moreover, it may also eventually be identified as allergy. In this manner, the LEMR element is important in itself, but the lifecycle of the element is equally important.

As a result, the LEMR may become a web of relationships, with a prevalent axis of time. The LEMR may capture information patient visit by patient visit, note during which visit the information is captured, and relate all such information to previous and future patient visits. In one variation, a "visit" may be equivalent to a patient encounter, or a patient episode of care, etc. In addition to this relative capacity, the LEMR may also be configured to summarize the patient's current health status in a single view such as a patient face sheet.

Elements within a LEMR may be discrete and codified. For example, a SOAP note as a text memo may not be a principal constituent of an LEMR, but many elements participating in capturing patient SOAP note information may be LEMR primary elements. The SOAP or progress note built from these elements is simply a data collection byprod-uct.

In one aspect, the LEMR may be supported by some form of office workflow. For example, without additional "cues," a LEMR may not specify the next patient encounter. How-ever, the LEMR design may include the ability to setup and collect information pointers directed at other activities within the LEMR. Such information pointers, also referred to as "tasks," may either be created before completing the patient encounter or by examining the state of a LEMR using Arden-syntax rules. This information pointer list may become the basis for care providers to effectively and accurately provide care to a patient.

Moreover, the LEMR may be configured to facilitate data collecting functions including, for example, the following:

Collect visit level information for administrative use such as demographic information, as well as clinical data such as subjective, objective, assessment and plan information.

Assume the management of follow up items. Any patient visit after the first patient visit should be geared toward following up on formulated or ordered plans from the previous visit.

Collect and maintain a list of patient items such as: problem list, medication list, plan list, etc.

Maintain item versioning: create over time a revision history of clinical items.

Implement a privacy protocol, such as HIPAA, which may include:

Providing an audit of all database activity, for insertions, updates and deletions. In other words, maintain "who did what and when."

Providing robust security. One layer (ADM, the bottom layer) may be central and may provide data and enforce security. All subsequent layers may be access layers, such as intelligent data access, business rule layer, presentation layer, interface layer(s), etc. In this con-figuration, the idea may be to divide and conquer, i.e. each layer may have specific responsibilities, not inter-fering with other layers, but combining to enhance security.

Providing role-based record access. The lowest layer (ADM) may define storage, security and data access roles. Roles may be defined to group together privi-leges: for example, being an administrator, or being a form application user, or being a report writer for all associated rights. Users may then be created and asso-ciated with roles. Applications may react on user login to enable a feature subject to authorization in accor-dance with a user's role, or possibly deny access to resources.

Forcing encryption on patient-sensitive data, both within the backend database and via any interface-type trans-missions.

Moreover, the LEMR may support secure data exchange and provide resource-based scheduling for appointments, tests, and other resource-based tasking. Further, the LEMR may be configured to provide a task-based workflow. Tasks are patient care workflow checkpoints. Completing a task may trigger the creation of further tasks and tasks may also be created by evaluating the current state of the patient using Arden Syntax-like rules, for example.

Intelligent Electronical Medical Record

The system may further interact with an intelligent elec-tronical medical record (iEMR). An iEMR may follow OHEAP (Orientation, History, Exam, Assessment and Plan)

as a model for how physicians manage patient care. For example, iEMR may be configured to:

Present a face sheet including, for example, information such as current medications, current allergies, and past immunizations.

Present metadata, instance data, and form internal hier-archy details.

Present script execution, and script source code.

iEMR may also provide a flexible infrastructure, allowing for ease of installation and customization. Further, it is contemplated that iEMR may be combined with an ADM engine for handling follow-up patient encounters. For example, iEMR may provide for a mix of rich client and thin client concepts for achieving optimal speeds during inter-actions.

Moreover, iEMR may be configured to support role-driven workflow; support knowledge object orientation; support dictionary lists; reduced source code necessary for building electronic medical record-type applications; sup-port lexicon knowledge queries; support task-based work-flow; provide rule scripting language geared toward health care; support macro operations; support document manage-ment functions; support pdf forms, pdf merge, pdf display; support rtf reports; support email workflow; and support hl7 communication services.

Exemplary Pipelines

Figure 9:
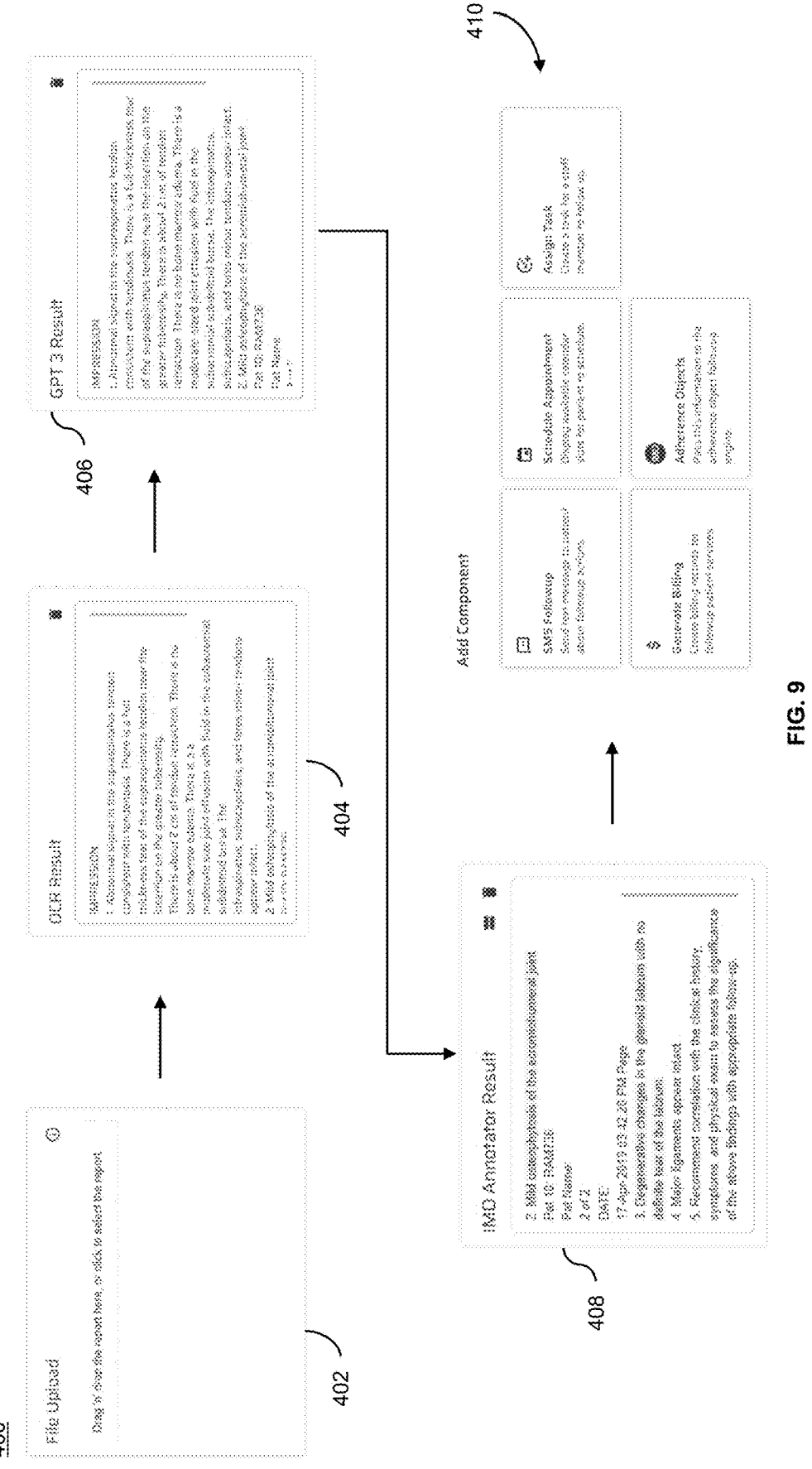
FIG. 9 illustrates an exemplary pipeline of system dynamically generate code or perform one or more actions.

FIG. 9 illustrates an exemplary pipeline 400 of system 100. As shown, system 100 may be configured to receive a file uploaded 402 by a user or accessible to the system. The file may be in any suitable format. Once uploaded, the system may be configured to recognize human-readable text within the file, such as via an optical character recognition (OCR) technique. An example of the OCR results 404 may be as follows:

Impression:

1. Abnormal signal in the supraspinatus tendon consistent with tendonosis. There is a full thickness tear of the supraspinatus tendon near the insertion on the greater tuberosity. There is about 2 cm of tendon retraction. There is no bone marrow edema. There is a moderate size joint effusion with fluid in the subacromial sub-deltoid bursa. The infraspinatus, subscapularis, and teres minor tendons appear intact.

2. Mild osteophytosis of the acromiohumeral joint.

Pat 10: RAM736

Pat Name:

DATE: 17 Apr. 2019 03:42:20 PM Page

3. Degenerative changes in the glenoid labrum with no definite tear of the labrum.

4. Major ligaments appear intact.

5. Recommend correlation with the clinical history, symp-toms, and physical exam to assess the significance of the above findings with appropriate follow up.

Results of the OCR may be input into an artificial-intelligence (AI) system, such as large language model (e.g., ChatGPT), to provide the following exemplary results 406:

Impression:

1. Abnormal signal in the supraspinatus tendon consistent with tendinosis. There is a full-thickness tear of the supraspinatus tendon near the insertion on the greater tuberosity. There is about 2 cm of tendon retraction. There is no bone marrow edema. There is a moderate-sized joint effusion with fluid in the subacromial sub-deltoid bursa. The infraspinatus, subscapularis, and teres minor tendons appear intact.

2. Mild osteophytosis of the acromiohumeral joint.

Pat 10: RAM736

Pat Name:

DATE: 17 Apr. 2019 03:42:20 PM Page

3. Degenerative changes in the glenoid labrum with no definite tear of the labrum.

4. Major ligaments appear intact.

5. Recommend correlation with the clinical history, symptoms, and physical exam to assess the significance of the above findings with appropriate follow-up.

As shown, the output of the language model may then be fed into an ontology tool 408 configured to use semantic annotation for ontology matching for evaluation by the system. Based on the results, system 100 may then be configured to dynamically generate code or perform one or more of the following actions 410:

1. SMS Follow-up: Send text message to patient about follow-up actions;

2. Schedule Appointment: Display available calendar slots for patient to schedule.

3. Assign Task: Create a task for a staff member to follow up.

4. Generate Billing: Create billing records for follow-up patient services.

5. Adherence Objects: Pass information to the adherence object component follow-up engine.

Exemplary Pipeline With Follow-Up Action

Figure 10:
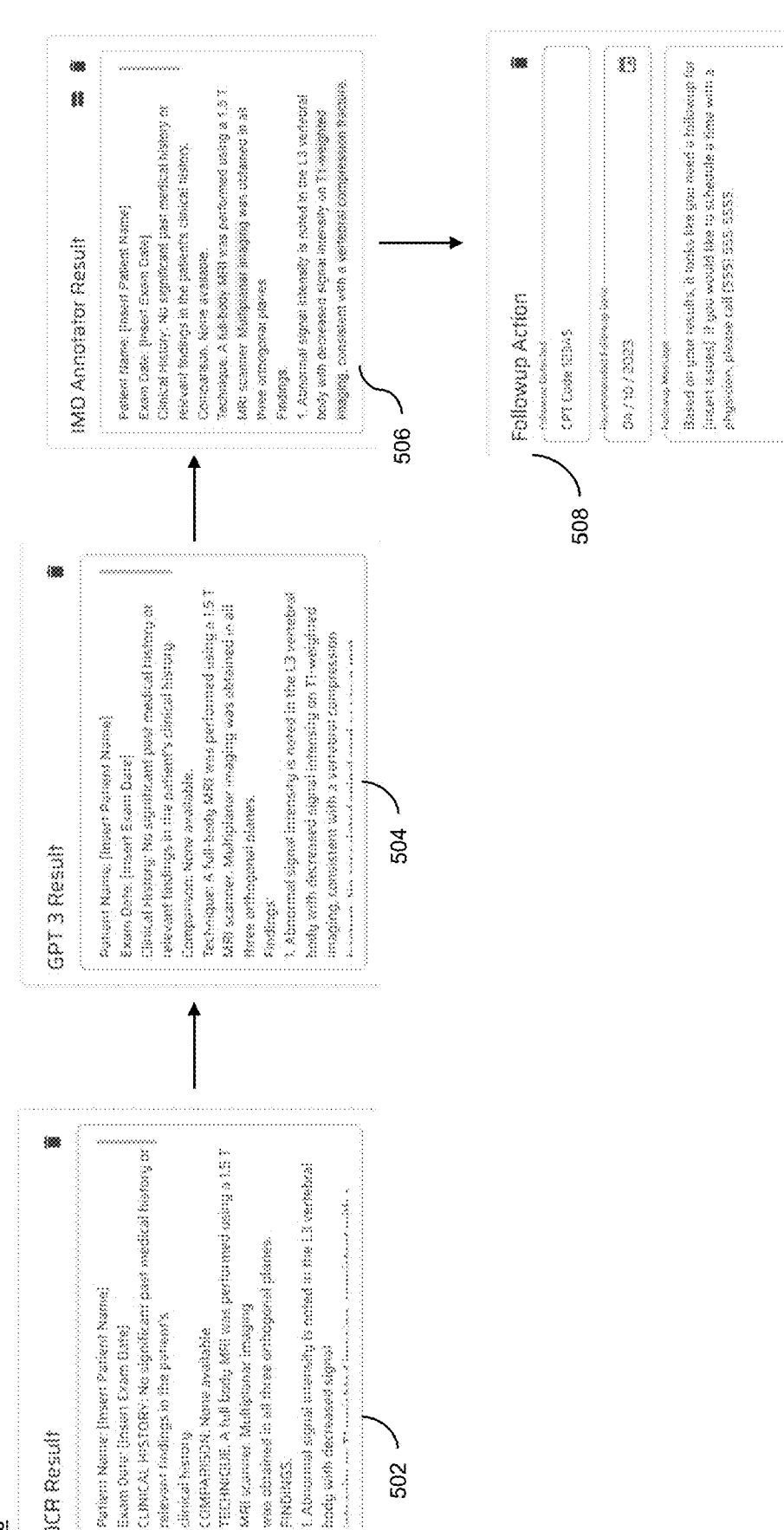
FIG. 10 illustrates another exemplary pipeline of the system including a follow-up action.

FIG. 10 illustrates another exemplary pipeline 500 of system 100 including a follow-up action. In particular, as above, system 100 may be configured to perform an optical character recognition (OCR) technique to recognize text, and output the following exemplary results 502:

Patient Name: [Insert Patient Name]

Exam Date: [Insert Exam Date]

CLINICAL HISTORY: No significant past medical history or relevant findings in the patient's clinical history.

COMPARISON: None available.

TECHNIQUE: A full body MRI was performed using a 1.5 T MRI scanner.

Multiplanar imaging was obtained in all three orthogonal planes.

Findings:

1. Abnormal signal intensity is noted in the L3 vertebral body with decreased signal intensity on T1 weighted imaging, consistent with a vertebral compression fracture. No associated spinal cord or nerve root impingement is identified.

2. The liver demonstrates multiple small hepatic lesions, with no clear evidence of malignancy on T1 T2 weighted imaging. Further evaluation with contrast-enhanced imaging is recommended.

3. A 1.5 cm complex cystic lesion is noted in the right kidney, which could represent a renal cyst or neoplastic lesion. Further evaluation with contrast-enhanced imaging is recommended.

4. The lungs demonstrate mild bibasilar atelectasis, which could represent small airway disease, pleural effusion or consolidation. Further evaluation with chest CT is recommended.

Impression:

1. Vertebral compression fracture at L3 without spinal cord or nerve root impingement.

2. Multiple small hepatic lesions, further evaluation with contrast-enhanced imaging recommended.

3. Complex cystic lesion in the right kidney, further evaluation with contrast-enhanced imaging recommended.

4. Mild bibasilar atelectasis in the lungs, further evaluation with chest CT recommended. The patient's findings are discussed with the referring physician, and further management is determined based on the additional imaging and clinical findings. [Insert Radiologist Signature and Credentials]

Results of the OCR may be input into an artificial-intelligence system, such as large language model, to provide the following exemplary results 504:

Patient Name: [Insert Patient Name]

Exam Date: [Insert Exam Date]

Clinical History: No significant past medical history or relevant findings in the patient's clinical history.

Comparison: None available.

Technique: A full-body MRI was performed using a 1.5 T MRI scanner.

Multiplanar imaging was obtained in all three orthogonal planes.

Findings:

1. Abnormal signal intensity is noted in the L3 vertebral body with decreased signal intensity on T1-weighted imaging, consistent with a vertebral compression fracture. No associated spinal cord or nerve root impingement is identified.

2. The liver demonstrates multiple small hepatic lesions, with no clear evidence of malignancy on T1-T2 weighted imaging. Further evaluation with contrast-enhanced imaging is recommended.

3. A 1.5 cm complex cystic lesion is noted in the right kidney, which could represent a renal cyst or neoplastic lesion. Further evaluation with contrast-enhanced imaging is recommended.

4. The lungs demonstrate mild bibasilar atelectasis, which could represent small airway disease, pleural effusion, or consolidation. Further evaluation with chest CT is recommended.

Impression:

1. Vertebral compression fracture at L3 without spinal cord or nerve root impingement.

2. Multiple small hepatic lesions, further evaluation with contrast-enhanced imaging recommended.

3. Complex cystic lesion in the right kidney, further evaluation with contrast-enhanced imaging recommended.

4. Mild bibasilar atelectasis in the lungs, further evaluation with chest CT recommended.

The patient's findings are discussed with the referring physician, and further management is determined based on the additional imaging and clinical findings.

[Insert Radiologist Signature and Credentials]

As shown, the results of the AI may then be fed into an ontology tool 506 configured to use semantic annotation for ontology matching for evaluation by the system. Based on the results, the system may then be configured to generate a follow-up action including the following exemplary text 508:

Based on your results, it looks like you need a followup for [insert issues]. If you would like to schedule a time with a physician, please call (555) 555-5555.

As above with regard to FIG. 9, the system may perform additional actions, such as assigning a task, generating a bill, and passing the information to another component of the system.

Mobile Applications and Customizable Personas

Figure 11:
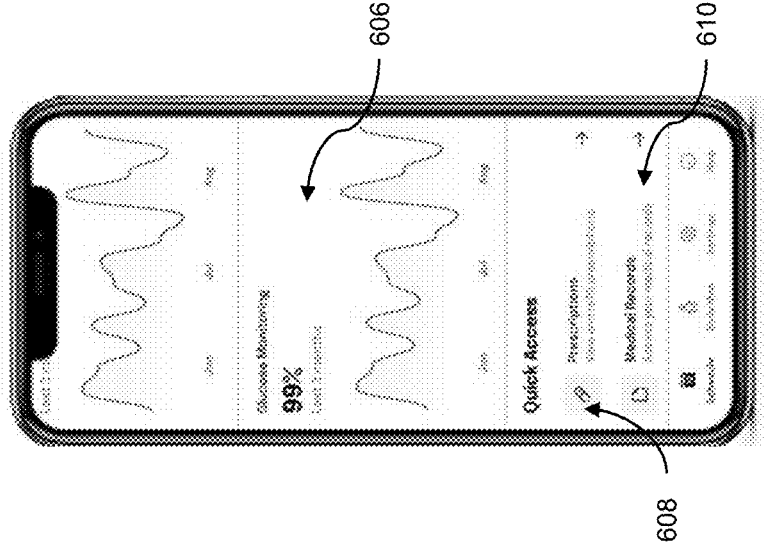
FIG. 11 illustrates screenshots of an exemplary mobile application of the system including a conversation or actionable artificial intelligence persona.
Figure 11:
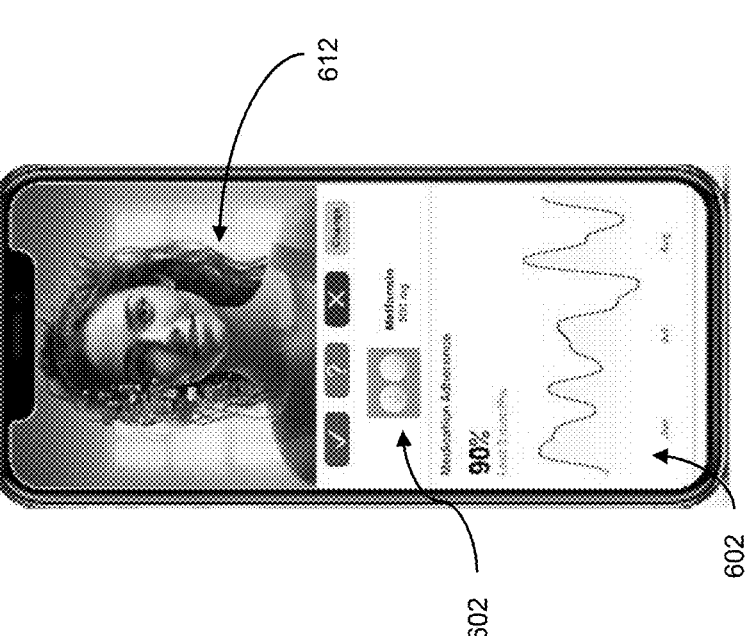
Figure 11:

FIG. 11 illustrates screenshots of an exemplary mobile application 600 of system 100. As shown, mobile application 600 may be configured to output patient-specific data from one or more components of system 100, such as adherence object component 102 and management therapy component 104. For example, application 600 may be configured to output the data as a chart or bar graph to display the patient's medication adherence 602 and detailed information on the medication to be taken 604. Further, application 600 may facilitate continuous glucose monitoring 606 and provide a user with access to patient prescriptions 608, medical records 610, and other information accessible to system 100.

As shown, mobile application 600 may further include a conversational or actionable artificial intelligence persona 612. Persona 612 may be customized or tailored to each user and patient. For instance, system 100 may automatically customize (e.g., by analyzing a user's actions and responses) persona 612 or the customization may be in response to user input preferences. Examples of customizable features of persona 612 may include appearance, tone, vocabulary, complexity, empathy, energy/frequency, and the like.

In one aspect of system 100, persona 612 may include a conversational bot module. Conversational bot module may be configured to convert a user's spoken input into a format that is usable by the other components of system 100 to determine an intent of the user. For example, conversational bot module may use natural language processing to convert the spoken input to data that represents adherence-related events that are useable by management therapy component 104 and adherence object component 102 to determine an adherence state of the patient, as described above. It is also contemplated that persona 612, through use of the conversational bot module, may be configured to perform cognitive analysis and/or artificial intelligence processes to, for example, converse, instruct, and/or coach a user according to one or more features of system 100 described above, such as patient-specific information, medication information, treatment adherence, corrective actions, scheduling, and the like.

In addition to conversing with a user, persona 612 may be configured to present the user with a visual representation of actions and events related to, for example, a patient's medication therapy plan. It is also contemplated that persona 612 may verify, monitor, generate and send to the user device screen shots relating to the patient's adherence, symptoms, and general health.

As mentioned above, persona 612 may be specific to each patient and the corresponding intelligence model trained based on the patient's age, symptoms, medical history, location, social background, financials, and the like. Persona 612 may also or in the alternative be trained using recorded research and researcher experience data, in addition to research paper content, tagging, metadata or indexing. Other techniques for training persona 612 are contemplated.

Exemplary Neural Network

Figure 12:
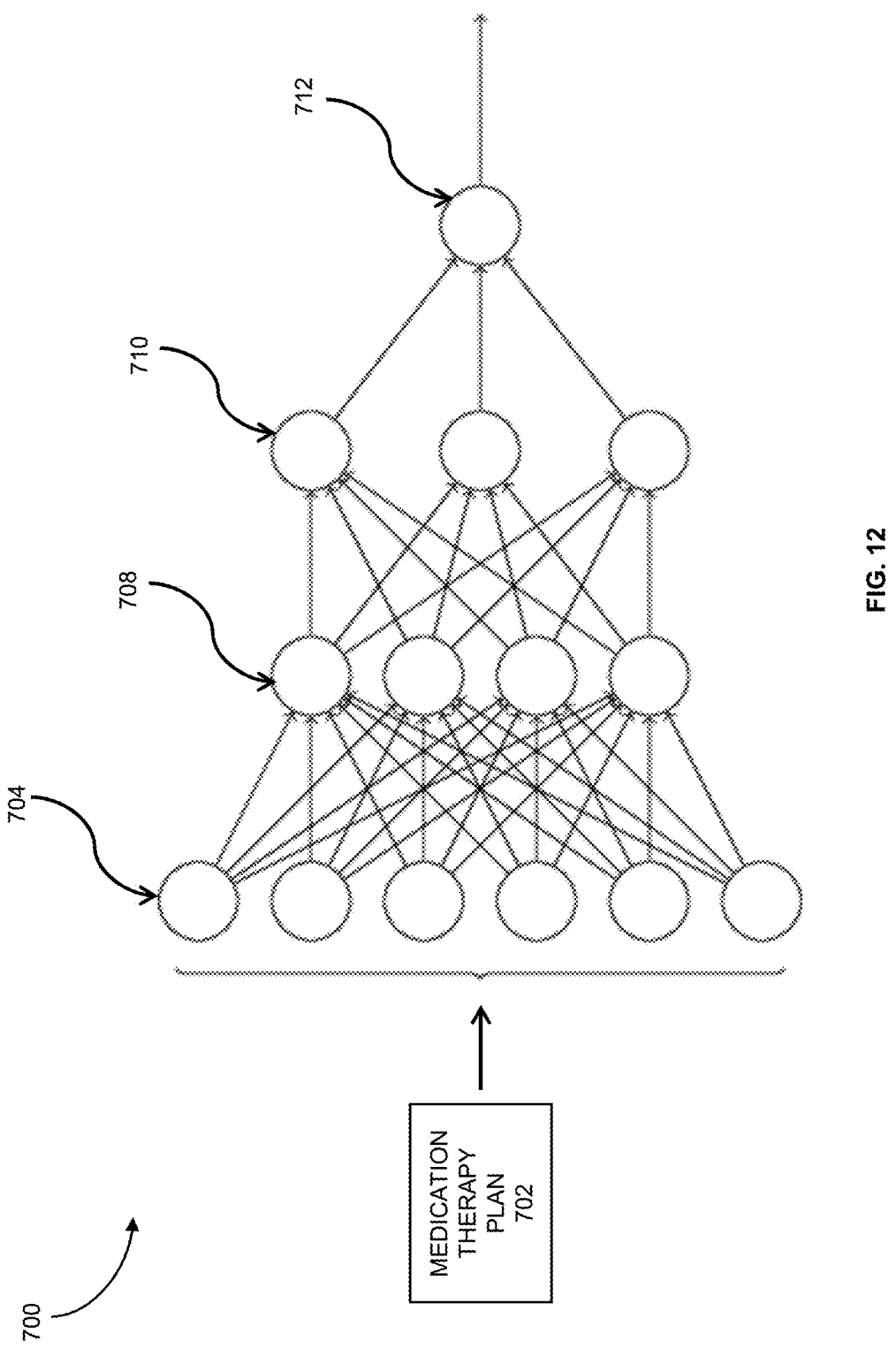
FIG. 12 illustrates an exemplary neural network that may be used to authenticate content.

FIG. 12 illustrates an exemplary neural network 700 that may be used to implement all or a portion of the methods according to the present invention. For example, the neural network 700 can be used to dynamically generate code to create events, drive next actions, and validate outcomes-based care corresponding to a patient's medical therapy plan.

As shown, network 700 may first segment therapy plan 702 into portions of data. The segmented data may then be input into a first layer 704—an input layer. Each layer in the neural network 700 is made up of neurons 706 that may include learnable weights and biases. The middle layers—for example, 708 and 710—are termed "hidden layers." Each hidden layer is fully connected to all neurons in the first input layer 704. The neurons in each single layer of the hidden layers 708, 710 function completely independently and do not share any connections. The last fully-connected layer 712 is termed the "output layer" and may represent an identified data element, such as a structured data element. In certain embodiments, the neural network 700 may be positioned between any two layers of a convolutional neural network such that the output layer 712 acts as an input into another layer of a neural network.

In this embodiment, the hidden layers 708, 710 neurons include a set of learnable filters, which can process portions of received therapy plan 702. As the therapy plan is processed across each filter, dot products are computed between the entries of the filter and the plan 702 to produce an activation map that gives the responses of that filter to the plan 702. The neural network 700 will learn filters that activate when they detect errors, perform optimization, and output the result.

Exemplary Computer System

Figure 13:
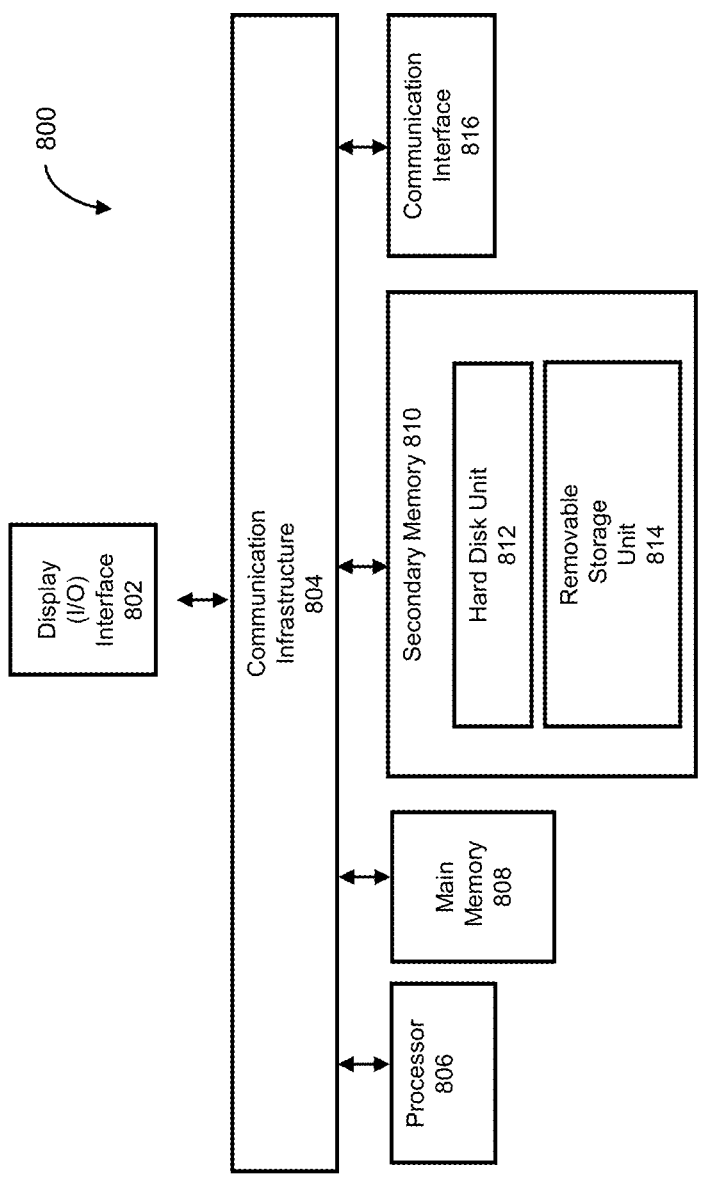
FIG. 13 is an exemplary computing system that may be used for implementation of all or a portion of the invention.

FIG. 13 illustrates a diagram of a system of which may be an embodiment of the present disclosure. System 800 includes an input/output interface 802 connected to communication infrastructure 804—such as a bus—which forwards data such as audio, graphics, text, and information, from the communication infrastructure 804 or from a frame buffer (not shown) to other components of the system 800. The input/output interface 802 may be a virtual reality, augmented reality or mixed reality device. Other examples of contemplated input/output interface may include a touchscreen, a display device, a keyboard, touch screen, joystick, trackball, mouse, monitor, speaker, printer, virtual and/or augmented reality unit, web camera, any other computer peripheral device, or any combination thereof, capable of inputting, receiving, and/or viewing data.

System 800 includes one or more processors 806, which may be a special purpose or a general-purpose digital signal processor configured to process certain information. System 800 also includes a main memory 808, for example random access memory (RAM), read-only memory (ROM), mass storage device, or combinations of each. System 800 may also include a secondary memory 510 such as a hard disk unit 512, a removable storage unit 514, or combinations of each. System 800 may also include a communication interface 516, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 808, secondary memory 510, communication interface 516, or combinations of each, function as a computer usable storage medium, otherwise referred to as a computer readable storage medium, to store and/or access computer software including computer instructions. For example, computer programs or other instructions may be loaded into the system 800 such as through a removable storage device, for example, a floppy disk, ZIP disks, magnetic tape, portable flash drive, optical disk such as a CD or DVD or Blu-ray, Micro-Electro-Mechanical Systems (MEMS), nano-technological apparatus. Specifically, computer software including computer instructions may be transferred from the removable storage unit 514 or hard disc unit 512 to the secondary memory 510 or through the communication infrastructure 803 to the main memory 808 of the system 800.

Communication interface 516 allows software, instructions and data to be transferred between the system 800 and external devices or external networks. Software, instructions, and/or data transferred by the communication interface 516 are typically in the form of signals that may be electronic, electromagnetic, optical or other signals capable of being sent and received by the communication interface 516. Signals may be sent and received using wire or cable, fiber optics, a phone line, a cellular phone link, a Radio Frequency (RF) link, wireless link, or other communication channels.

Computer programs, when executed, enable system 800, particularly the processor 806, to implement the disclosed methods according to computer software including instructions.

System 800 described may perform any one of, or any combination of, the steps of any of the methods according to the invention. It is also contemplated that the methods according to the invention may be performed automatically.

The system 800 of FIG. 13 is provided only for purposes of illustration, such that the invention is not limited to this specific embodiment. It is appreciated that a person skilled in the relevant art knows how to program and implement the invention using any computer system.

System 800 may be a handheld device and include any small-sized computer device including, for example, a personal digital assistant (PDA), hand-held computing device, cellular telephone, or a laptop or netbook computer, mobile system, tablet, or similar handheld computer device, such as an iPad, iPad Touch or iPhone.

Exemplary Cloud Computing System

Figure 14:
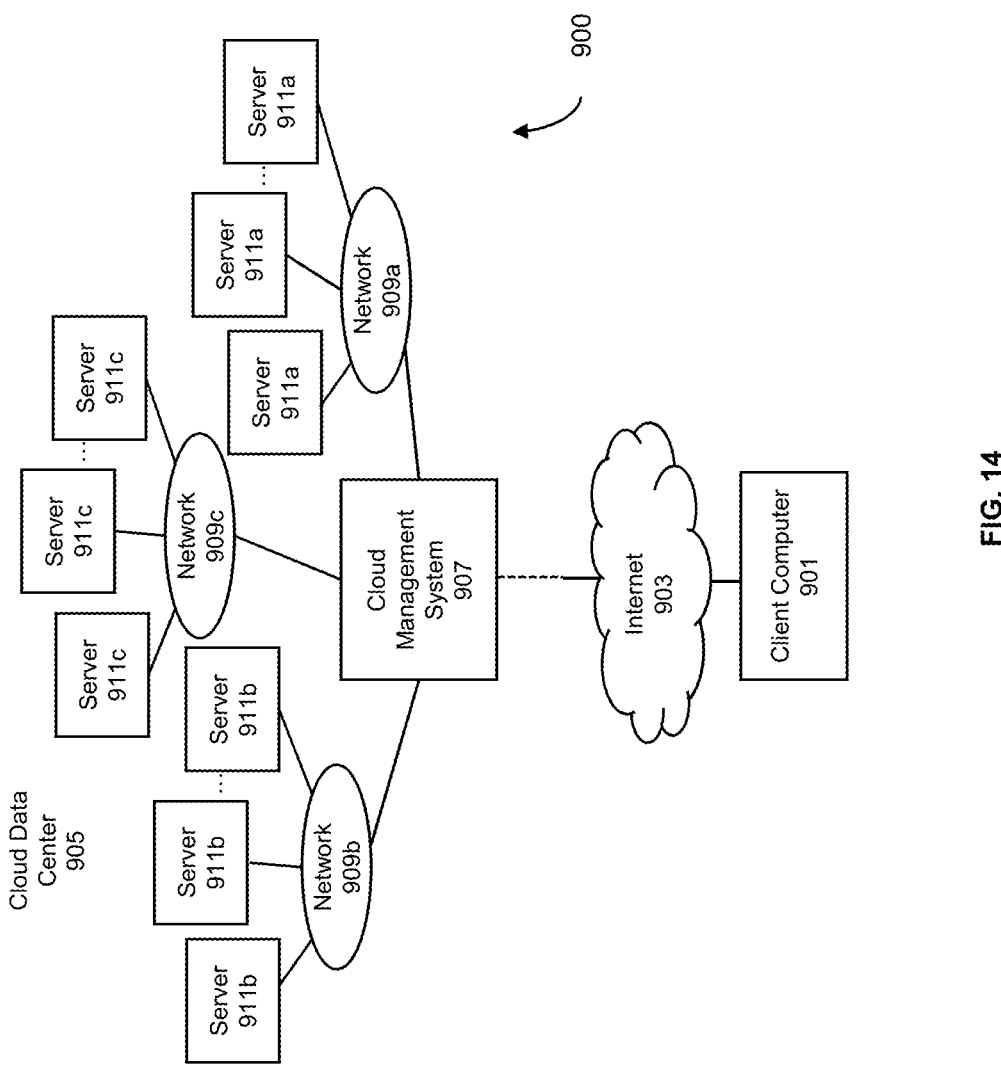
FIG. 14 is an exemplary cloud computing system that may be used for implementation of all or a portion of the invention.

FIG. 14 illustrates an exemplary cloud computing system 900 that may be an embodiment of the present invention. The cloud computing system 900 includes a plurality of interconnected computing environments. The cloud computing system 900 utilizes the resources from various networks as a collective virtual computer, where the services and applications can run independently from a particular computer or server configuration making hardware less important.

Specifically, the cloud computing system 900 includes at least one client computer 901. The client computer 901 may be any device through the use of which a distributed computing environment may be accessed to perform the methods disclosed herein, for example, a traditional computer, portable computer, mobile phone, personal digital assistant, tablet to name a few. The client computer 901 includes memory such as random access memory (RAM), read-only memory (ROM), mass storage device, or any combination thereof. The memory functions as a computer usable storage medium, otherwise referred to as a computer readable storage medium, to store and/or access computer software and/or instructions.

The client computer 901 also may include a communications interface, for example, a modem, a network interface (such as an Ethernet card), a communications port, a PCM-CIA slot and card, wired or wireless systems, etc. The communications interface allows communication through transferred signals between the client computer 901 and external devices including networks such as the Internet 903 and cloud data center 905. Communication may be implemented using wireless or wired capability such as cable, fiber optics, a phone line, a cellular phone link, radio waves or other communication channels.

The client computer 901 establishes communication with the Internet 903—specifically to one or more servers—to, in turn, establish communication with one or more cloud data centers 905. A cloud data center 905 includes one or more networks 909*a*, 909*b*, 909*c* managed through a cloud management system 907. Each network 909*a*, 909*b*, 909*c* includes resource servers 911*a*, 911*b*, 911*c*, respectively.

Servers 911*a*, 911*b*, 911*c* permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 907 can comprise a dedicated or centralized server and/or other software, hardware, and network tools to communicate with one or more networks 909*a*, 909*b*, 909*c*, such as the Internet or other public or private network, with all sets of resource servers 911*a*, 911*b*, 911*c*. The cloud management system 907 may be configured to query and identify the computing resources and components managed by the set of resource servers 911*a*, 911*b*, 911*c* needed and available for use in the cloud data center 905. Specifically, the cloud management system 907 may be configured to identify the hardware resources and components such as type and amount of processing power, type and amount of memory, type and amount of storage, type and amount of network bandwidth and the like, of the set of resource servers 911*a*, 911*b*, 911*c* needed and available for use in the cloud data center 905. Likewise, the cloud management system 907 can be configured to identify the software resources and components, such as type of Operating System (OS), application programs, and the like, of the set of resource servers 911*a*, 911*b*, 911*c* needed and available for use in the cloud data center 905.

The present invention is also directed to computer products, otherwise referred to as computer program products, to provide software to the cloud computing system 900. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems (MEMS), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 900 of FIG. 14 is provided only for purposes of illustration and does not limit the invention to this specific embodiment. It is appreciated that a person skilled in the relevant art knows how to program and implement the invention using any computer system or network architecture.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described in the application are to be taken as examples of embodiments. Components may be substituted for those illustrated and described in the application, parts and processes may be reversed, and certain features of the invention may be utilized independently, all as would be apparent to one skilled in the art after having the benefit of this description of the invention. Changes may be made in the elements described in the application without departing from the spirit and scope of the invention as described in the following claims.

What is claimed is:

1. A system for medication therapy management, comprising:
   a processor;
   a main memory in communication with the processor via a communication infrastructure, the main memory including stored instructions that, when executed by the processor, cause the processor to:
      access a medical record of a patient and store a structured data set, wherein accessing the medical record includes integrating with an electronic health record including at least one of clinical data and genomic data;
      analyze the structured data set, wherein the structured data set identifies one or more orders corresponding to a diagnosis, wherein the one or more orders comprises one or more of a scheduled medication or therapy plan;
      store one or more events corresponding the structured data set;
      store a patient state in response to receiving an input corresponding to the one or more events; and
      output a user interface corresponding to at least one of the medical record, the one or more events, and the patient state and the user interface comprising a graph of medication adherence as a time series and a conversational bot displayed with a persona comprising a customizable appearance.

2. The system of claim 1, wherein analyzing the structured data set includes prepopulating a medication therapy plan.

3. The system of claim 1, wherein storing the one or more events includes dynamically generating code in response to identifying the one or more orders.

4. The system of claim 3, wherein the generated code includes questionnaires corresponding to at least one of the patient, the one or more orders, and the diagnosis.

5. The system of claim 1, wherein storing the one or more events includes dynamically generating code corresponding to one or more connected devices of the patient.

6. The system of claim 5, wherein storing the patient state includes retrieving behavior data from the one or more connected devices, the behavior data corresponding to at least one of a patient's diet, emotional state, sleep, and exercise.

7. The system of claim 1, wherein storing the patient state includes monitoring medication compliance, questionnaires, alerts, and notifications.

8. The system of claim 1, wherein the one or more patient states includes at least one of adherent, non-adherent, patient adverse event, provider intervention, additional analysis request, and end of treatment.

9. The system of claim 1, wherein outputting the user interface includes displaying a care management dashboard associated with at least one of severity and management status, categorized problems lists and past medical history, allergy intolerance, and social and family history.

10. The system of claim 9, wherein the care management dashboard includes at least one of a descriptive component, a graphical component, and a temporal element relating to the diagnosis.

11. The system of claim 9, wherein the care management dashboard is configured to output a timeline of the events and received inputs.

12. The system of claim 1, wherein each order may include a designated protocol corresponding to the diagnosis.

13. The system of claim 1, wherein the one or more events corresponds to a scheduled time period for complying with the one or more orders.

14. The system of claim 1, wherein the processor is configured to customize attributes of the persona based on patient preferences.

15. The system of claim 14, wherein the persona is configured to perform cognitive analysis and artificial intelligence processes to converse, instruct, and coach using at least one of patient-specific information, medication information, treatment adherence, corrective actions, and scheduling.

16. A method for medication therapy management, comprising:
   accessing a database including clinical and genomic data corresponding to a patient;
   storing a structured data set based on the clinical and genomic data;
   analyzing the structured data set, wherein the structured data set identifies one or more medication therapy plans corresponding to a diagnosis;
   storing one or more events corresponding the structured data set based on a set of rules associated with the one or more medication therapy plans;
   storing a patient state in response to receiving an input corresponding to the one or more events; and
   output, via a graphical user interface, at least one of a patient medical record, the one or more events, and the patient state, wherein the graphical user interface comprises a graph of medication adherence as a time series and a conversational bot displayed with a persona comprising a customizable appearance.

17. The method of claim 16, wherein storing the one or more events includes dynamically generating code corresponding to behavior data retrieved from one or more connected devices of the patient, the behavior data corresponding to at least one of a patient's diet, emotional state, sleep, and exercise.

18. The method of claim 16, wherein the patient state is identified as one of adherent, non-adherent, patient adverse event, provider intervention, additional analysis request, and end of treatment.

19. The method of claim 16, wherein outputting via the graphical user interface comprises displaying the persona configured to perform cognitive analysis and artificial intelligence processes to converse, instruct, and coach using at least one of patient-specific information, medication information, treatment adherence, corrective actions, and scheduling.

\* \* \* \* \*